US007251609B1

(12) United States Patent
McAlindon et al.

(10) Patent No.: US 7,251,609 B1
(45) Date of Patent: Jul. 31, 2007

(54) METHOD FOR CONDUCTING CLINICAL TRIALS OVER THE INTERNET

(75) Inventors: Timothy E. McAlindon, Belmont, MA (US); Karim A. N. Kabbara, Weymouth, MA (US)

(73) Assignee: The Trustees of Boston University, Boston, MA (US)

( * ) Notice: Subject to any disclaimer, the term of this patent is extended or adjusted under 35 U.S.C. 154(b) by 0 days.

(21) Appl. No.: 09/560,597

(22) Filed: Apr. 28, 2000

Related U.S. Application Data

(60) Provisional application No. 60/131,528, filed on Apr. 29, 1999.

(51) Int. Cl.
*G06F 19/00* (2006.01)

(52) U.S. Cl. .............................. 705/3; 600/300; 707/9; 434/322

(58) Field of Classification Search ................ 705/2, 705/3; 600/300; 707/1, 9
See application file for complete search history.

(56) References Cited

U.S. PATENT DOCUMENTS

| 5,991,731 A * | 11/1999 | Colon et al. ................... 705/2 |
| 6,047,259 A * | 4/2000 | Campbell et al. ............... 705/2 |
| 2002/0035486 A1* | 3/2002 | Huyn et al. ..................... 705/3 |
| 2003/0055679 A1* | 3/2003 | Soll et al. ....................... 705/2 |

FOREIGN PATENT DOCUMENTS

WO    WO 98/52113    11/1998

OTHER PUBLICATIONS

Hopp, David I, "Three topics integral to the use of the Internet for clinical trials: Connectivity, communication, and security," Drug Information Journal, Oct.-Dec. 1999.*

Brin, Dinah, "Lilly warns Nutri System about using Prozac," The Patriot Ledger, Sep. 17, 1997, pp. 5-6.*

Davis, Terry, Holcombe, Randall, Berkel, Hans, Pramanik, Sumona, and Divers, Stephen G., "Informed consent for clinical trials: A comparative study of standard versus simplified forms," Journal of the National Cancer Institute, May 6, 1998, pp. 668-674.*

Hopp, David I, "Three topics integral to the use of the Internet for clinical trials: Connectivity, communication, and security," Drug Information Journal, Oct.-Dec. 1998.*

Brin, Dinah, "Lilly warns Nutri System about using Prozac," The Patriot Ledger, Sep. 17, 1997, pp. 5-6.*

Vincent J. Carey "Using Hypertext and The Internet For Structure and Management of Observational Studies", Statistics in Medicine, vol. 16, pp. 1667-1682 (1997).

(Continued)

*Primary Examiner*—C. Luke Gilligan
*Assistant Examiner*—Rachel L Porter
(74) *Attorney, Agent, or Firm*—Weingarten, Schurgin, Gagnebin & Lebovici LLP

(57) ABSTRACT

The invention encompasses a method of conducting a clinical trial of a test substance from a primary site, via the internet. The internet is used in various phases of a clinical trial, including: recruiting and screening for candidates who are eligible to participate in a clinical trial of a test substance using the internet; obtaining, directly from a participant at a remote site, personal information as well as information allowing a determination of any effect(s) of the test substance on the participant after use (e.g., by evaluation forms completed and transmitted over the internet); compiling data from multiple participants.

35 Claims, 11 Drawing Sheets

OTHER PUBLICATIONS

D. John Doyle et al. "Symposium: A Clinician's Guide To The Internet", Yale Journal of Biology and Medicine 69 pp. 429-437. (1996).

Lawrence H. Kushi et al., Letter to the Editor re "Epidermiology and the Internet," Epidemiology, vol. 8, No. 6 pp. 689-670. Nov. (1997).

Robert H. Friedman, MD, et al. "The Virtual Visit: Using Telecommunications Technology to Take Care of Patients" Journal of the American Medical Informatics Associations, vol. 4, No. 6, Nov./Dec. 1997, pp. 413-425.

Jeffrey D. Houston, M.D., et al. "Online Medical Surveys: Using the Internet as a Research Tool", M.D. Computing, vol. 15, No. 2, pp. 116-120 (1998).

Kenneth J. Rothman et al., "Epidemiology and the Internet" Epidemiology vol. 8, No. 2 pp. 123-125 (Mar. 1997).

Kenneth D. Mandl, MD, et al. "Electronic Patient-Physician Communication: Problems and Promise" Annals of Medicine vol. 129, No. 6, pp. 495-500 (1998).

Caroline McNeil, "Marketing Clinical Trials on The Internet", Journal of the National Cancer Institute vol. 88, No. 20, p. 1435 Oct. 16, 1996.

M.A. Kelly et al. "The Internet and randomised controlled trials", International Journal of Medical Informatics vol. 47, pp. 91-99 (1997).

Roy M. Soetikno M.D., et al. "Studying Ulcerative Colitis Over the World Wide Web", The American Journal of Gastroenterology vol. 92. No. 3, (1997).

Roy M. Soetikno M.D., et al. "Quality-Of-Life Research on the Internet . . . " Journal of Medical Informatics Association. vol. 4 pp. 426-433, (1997).

Stanford Arthritis and Rheumatology Research website on Apr. 6, 1999, advertising traditional clinical trial and surveys.

Genelabs Technologies's website on Apr. 6, 1999, advertising traditional clinical trial for phase III trial of GL701 compound for SLE.

University of Pennsylvania Veterinary Hospital's website on Mar. 25, 1999, with Oncolink Clinical Trial Announcement.

University of Pennsylvania Cancer Center's Clinical Trials News website on Mar. 25, 1999, listing traditional cancer related Phase I-III.

Kansas City Clinical Oncology Program website on Mar. 25, 1999, advertising a Phase III Trial and posting a consent form.

Aids Clinical Trials website on Apr. 9, 1999, providing full texts of protocols of major clinical trials networks.

* cited by examiner

Overview of the trial process.
Filled boxes represent Web pages.
Ellipses represent decisions and actions.

| ONLINE GLUCOSAMINE TRIAL | HELP | BOSTON UNIVERSITY SCHOOL of Medicine |

- ONLINE VISITS
- YOUR SCHEDULE
- REPORT SIDE-EFFECTS
- QUESTIONS?
- COMMENTS?
- LOGOUT

Welcome to your First Visit

SECTION A:
The following questions concern the amount of pain you have experienced due to arthritis in your knee(s). For each situation please enter the amount of pain experienced in the last 48hrs.

*QUESTION: How much pain do you have?*

1. Walking on a flat surface.

| None | Mild | Moderate | Severe | Extreme |
|------|------|----------|--------|---------|
| O | O | O | O | O |

2. Going up or down stairs.

| None | Mild | Moderate | Severe | Extreme |
|------|------|----------|--------|---------|
| O | O | O | O | O |

3. At night while in bed?

| None | Mild | Moderate | Severe | Extreme |
|------|------|----------|--------|---------|
| O | O | O | O | O |

4. Sitting or lying?

| None | Mild | Moderate | Severe | Extreme |
|------|------|----------|--------|---------|
| O | O | O | O | O |

5. Standing upright?

| None | Mild | Moderate | Severe | Extreme |
|------|------|----------|--------|---------|
| O | O | O | O | O |

SECTION B:
The following questions concern the amount of joint stiffness (not pain) you have experienced in the last 48 hours in your knee(s). Stiffness is a sensation of restriction or slowness in the ease with which you move your joints.

*QUESTION: How severe is your stiffness?*

6. After first wakening in the morning?

| None | Mild | Moderate | Severe | Extreme |
|------|------|----------|--------|---------|
| O | O | O | O | O |

7. After sitting, lying or resting later in the day?

| None | Mild | Moderate | Severe | Extreme |
|------|------|----------|--------|---------|
| O | O | O | O | O |

*FIG. 8A*

SECTION C:
The following questions concern your physical functions. By this we mean your ability to move around and look after yourself. For each of the following activities, please indicate the degree of difficulty you have experienced in the last 48 hours due to arthritis in your knee(s).

*QUESTION: What degree of difficulty do you have?*

8. Going down the stairs?
| None | Mild | Moderate | Severe | Extreme |
|---|---|---|---|---|
| O | O | O | O | O |

9. Going up the stairs?
| None | Mild | Moderate | Severe | Extreme |
|---|---|---|---|---|
| O | O | O | O | O |

10. Rising from sitting?
| None | Mild | Moderate | Severe | Extreme |
|---|---|---|---|---|
| O | O | O | O | O |

11. Standing?
| None | Mild | Moderate | Severe | Extreme |
|---|---|---|---|---|
| O | O | O | O | O |

12. Bending to the floor?
| None | Mild | Moderate | Severe | Extreme |
|---|---|---|---|---|
| O | O | O | O | O |

13. Walking on a flat surface?
| None | Mild | Moderate | Severe | Extreme |
|---|---|---|---|---|
| O | O | O | O | O |

14. Getting in/out of a car?
| None | Mild | Moderate | Severe | Extreme |
|---|---|---|---|---|
| O | O | O | O | O |

15. Going shopping?
| None | Mild | Moderate | Severe | Extreme |
|---|---|---|---|---|
| O | O | O | O | O |

16. Putting on socks/stockings?
| None | Mild | Moderate | Severe | Extreme |
|---|---|---|---|---|
| O | O | O | O | O |

17. Rising from bed?
| None | Mild | Moderate | Severe | Extreme |
|---|---|---|---|---|
| O | O | O | O | O |

18. Taking off socks/stockings?
| None | Mild | Moderate | Severe | Extreme |
|---|---|---|---|---|
| O | O | O | O | O |

*FIG. 8B*

19. Lying in bed?

| None | Mild | Moderate | Severe | Extreme |
|------|------|----------|--------|---------|
| O    | O    | O        | O      | O       |

20. Getting in/out of the bath?

| None | Mild | Moderate | Severe | Extreme |
|------|------|----------|--------|---------|
| O    | O    | O        | O      | O       |

21. Sitting?

| None | Mild | Moderate | Severe | Extreme |
|------|------|----------|--------|---------|
| O    | O    | O        | O      | O       |

22. Getting on/off toilet?

| None | Mild | Moderate | Severe | Extreme |
|------|------|----------|--------|---------|
| O    | O    | O        | O      | O       |

23. Doing heavy domestic duties?

| None | Mild | Moderate | Severe | Extreme |
|------|------|----------|--------|---------|
| O    | O    | O        | O      | O       |

24. Doing light domestic duties?

| None | Mild | Moderate | Severe | Extreme |
|------|------|----------|--------|---------|
| O    | O    | O        | O      | O       |

Important:

1. You may take your usual painkillers for your knees if you need them. However, we need you to keep a record of how many painkillers you take each day. We will ask you for this number at each of your visits.

2. Also, we ask that you stick to the same painkiller for the length of the study.

Please enter the name of the painkiller that you usually take for your knee-pain (eg ibuprofen, Motrin, Tylenol):

This is the painkiller that we will expect you to use during the study for breakthrough pain Please enter your current height (feet and inches)  [4 ▽] ' [0 ▽] "

Please enter your current weight (pounds)  [0]

[Submit]  [Clear]

*FIG. 8C*

ONLINE GLUCOSAMINE TRIAL  HELP  BOSTON UNIVERSITY SCHOOL of Medicine

- ONLINE VISITS
- YOUR SCHEDULE
- REPORT SIDE-EFFECTS
- QUESTIONS?
- COMMENTS?
- LOGOUT

Welcome to your Second Visit

The following questions concern the amount of pain you have experienced due to arthritis in your knee(s). For each situation please enter the amount of pain experienced in the last 48hrs.

*QUESTION: How much pain do you have?*

1. Walking on a flat surface.

| None | Mild | Moderate | Severe | Extreme |
   |---|---|---|---|---|
   | ○ | ○ | ○ | ○ | ○ |

2. Going up or down stairs.

| None | Mild | Moderate | Severe | Extreme |
   |---|---|---|---|---|
   | ○ | ○ | ○ | ○ | ○ |

3. At night while in bed?

| None | Mild | Moderate | Severe | Extreme |
   |---|---|---|---|---|
   | ○ | ○ | ○ | ○ | ○ |

4. Sitting or lying?

| None | Mild | Moderate | Severe | Extreme |
   |---|---|---|---|---|
   | ○ | ○ | ○ | ○ | ○ |

5. Standing upright?

| None | Mild | Moderate | Severe | Extreme |
   |---|---|---|---|---|
   | ○ | ○ | ○ | ○ | ○ |

Other questions:

6. How many cigarettes do you smoke on average each day?
   - ⦿ None
   - ○ Less than 5 per day
   - ○ 4-14 per day
   - ○ 15-24 per day
   - ○ 25 or more per day 6. How many alcoholic beverages do you drink on average each week?
   - ⦿ None
   - ○ Less than 1
   - ○ 1-3
   - ○ 4-6
   - ○ 7-13
   - ○ 14-20
   - ○ 21 or more 8. Please tell us how many of your usual painkillers you have taken since your last completed visit.

[        ]

[ Submit ]  [ Clear ]

*FIG. 9*

METHOD FOR CONDUCTING CLINICAL TRIALS OVER THE INTERNET

CROSS REFERENCE TO RELATED APPLICATIONS

This application claims priority from U.S. Provisional Application No. 60/131,528, filed on Apr. 29, 1999, which is incorporated herein by reference.

STATEMENT REGARDING FEDERALLY SPONSORED RESEARCH OR DEVELOPMENT

This invention was made with U.S. Government Support under Contract Number 1RO1LM06856-01, awarded by the National Institutes of Health. The Federal Government therefore has certain rights in the invention.

BACKGROUND OF THE INVENTION

The invention relates to the use of the internet in medical and clinical research.

The conduct of trials for a new drug, food supplement or other human or animal intended preparation is typically done through clinical trials. Conventionally, clinical trial participants are monitored at one or more central site(s), such as a doctor's office, clinic, hospital, or other health care facility. The participants are either institutionalized at or must make regular visits to such a facility to be checked, to receive new medications, or to otherwise consult with the trial's principal investigators and their assistants. The trials typically involve more than one substance being administered: at least one being a test substance—i.e., a compound or preparation having a hoped-for effectiveness—and at least one being a placebo or control substance. Multiple test substances of expected effectiveness are often used.

The requirement for regular appearance of participants at a monitoring facility has a number of disadvantages, particularly for trials for interventional drugs. These disadvantages include the burden on the researchers and/or their assistants to spend time scheduling visits, to conduct interviews with each participant, and to compile data on the effectiveness of each substance undergoing test. This burden is magnified by the number of substances and placebos involved in the trial. The need for a large number of participants for statistical accuracy further increases the burden, both in terms of time and resources. Conventional trials having many participants also usually involve multiple test facilities, and staff and resources at each facility in order to conduct the trial there.

Moreover, the scheduling of participant visits is based on information and other factors that are not necessarily interactive with the participant, and thus visits may be at inappropriate or inconvenient times. This can lead to inadequate participant monitoring and/or to non-compliance with a trial protocol, which may adversely affect the accuracy of clinical trial results.

Because of the time burden on the research staff and the ineffectiveness of the timing of visits or data acquisition from the participants, it is nearly impossible to test a large number of drugs in a single, conventionally conducted trial in order to have a more effective way of drug comparison.

The need for the participants to travel to the monitoring facility is also a burden on their time and produces results that can be biased by having data collected in other than a relaxed, customary or home setting. This travel also prevents the data being given and taken in real time or close to the actual time of the participant's observations that are the basis of the data gathered in the trial. Such a time lag can also affect the accuracy of the information gathered and bias the trial results.

The present invention addresses the preceding problems of conventional clinical trials, through a heretofore unexplored medical application of the internet. The invention encompasses conducting major, even all, aspects of a clinical trial on-line, including direct monitoring or evaluation of trial participants. Because of the vast scope of the internet, it may be possible to study the attributes of a wide variety of compounds, including ones that are difficult or impractical to evaluate in traditional clinical trial formats, which typically use clinic-based settings, often at multiple clinics. For example, there exist a number of nutritional compounds or food supplements (commonly called "nutriceuticals") that may be modestly effective in relieving symptoms of a non-life-threatening condition. Because of the large numbers of participants required and of the prohibitive costs involved in detecting efficacy from these compounds, it is unlikely that they will all be adequately evaluated by traditional, clinic-based trials. On the other hand, the internet, through use of validated symptom-monitoring questionnaires, can have great utility in facilitating the effective and economical testing of non-toxic, safe compounds in the treatment of various conditions, e.g., osteoarthritis.

Some publications have explored the potential of the internet for facilitating purely observational, epidemiological studies and describe how recent software developments can be used to enhance data security, allow automated data compilation and evaluate in-coming data in real-time. [i,ii,iii] The internet has also been proposed as a vehicle for facilitating the conduct of large, multi-center, conventional clinical trials by allowing global access to collected data, fast interaction with the database and automation of some aspects of data collection and manipulation[iv]. However, until the present invention, there has been no suggestion to use the internet to direct and monitor, from a central site, the administration of an interventional test substance to trial participants at remote sites.

BRIEF SUMMARY OF THE INVENTION

The method of the invention relates to use of the internet in conducting a clinical trial of the effectiveness of a test substance administered to a clinical trial participant. The trial is conducted from a primary internet site providing a centralized location from which the trial investigator(s) direct and monitor the clinical trial. From this primary site, the trial investigator(s) directs and evaluates the use of the test substance by a clinical trial participant at a remote site, via the internet. Thus, the internet can be used in a cost-effective manner to carry out one or more phases of a clinical trial of a test substance.

Suitable test substances include, but are not limited to, safe, non-prescription substances (nutritional or food compounds or "nutriceuticals") that might be effective to treat a medical condition, especially a non-life-threatening one (e.g., arthritis). Test substances can also encompass over-the-counter medications, as well as certain FDA-approved, prescription-only medications.

The internet is used to perform key aspects of the clinical trial. These include: advertising and providing information about the clinical trial; screening for and recruiting eligible participants in the clinical trial; evaluating and monitoring clinical trial results from participants at sites remote from the investigator(s) conducting the trial; obtaining, compiling, and verifying information from each clinical trial participant; and distributing trial results.

The Internet is first used as a medium for advertising the trial and solicitation of candidate participants for a proposed clinical trial of one or more test substances. Responses from likely candidates are followed up with a questionnaire that the candidate completes and returns, again via the internet.

The researchers process the application and test the responses to the questionnaire against a reference standard as a part of qualifying the candidates. Computational algorithms can be used for this purpose. The candidates that are qualified to participate are given notice, access codes, and passwords, and are requested to provide, via the internet or other medium, informed consent for their participation in the trial and for access to their medical records.

Participation begins with or without preliminary statistical procedures. Participants are supplied with at least one drug to be used and are required to conduct online interviews or questionnaire submissions periodically to the trial investigator(s), to provide data that will be used in the evaluation of the drug's effectiveness. The data are collected and processed in a manner devised by researchers to provide the analyses desired, including the comparison of several drugs and placebos used in the trial, as appropriate.

BRIEF DESCRIPTION OF THE SEVERAL VIEWS OF THE DRAWING

FIGS. 8A-8C depict an exemplary webpage containing a first-visit evaluation form; and FIG. 9 depicts an exemplary webpage containing a second-visit evaluation form.

DETAILED DESCRIPTION OF THE INVENTION

The method of the invention encompasses performing anywhere from just a few steps up to essentially all steps of a clinical trial, via the internet.

Figure 1:
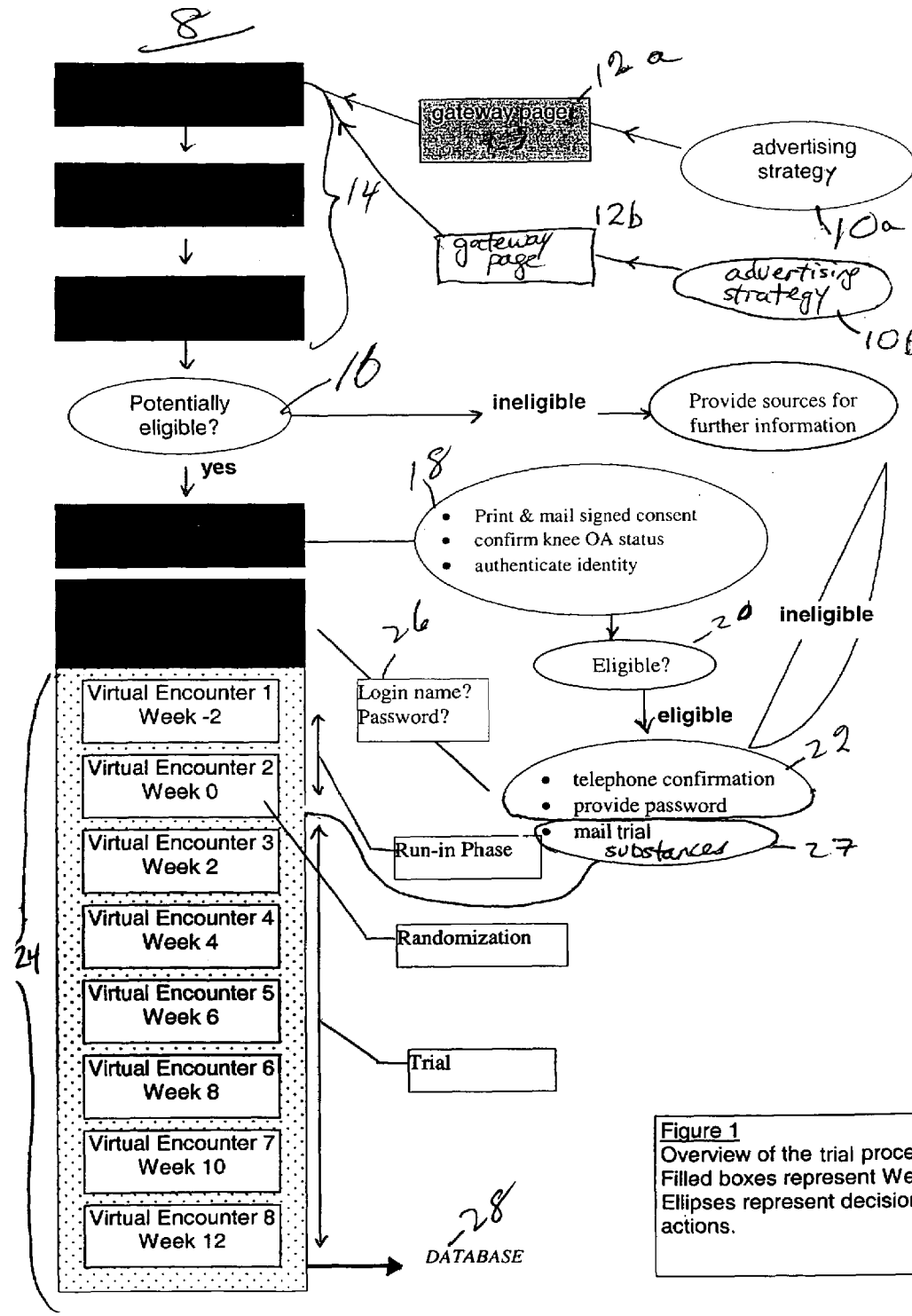
FIG. 1 is a schematic flow chart of the invention's method of conducting a clinical trial over the internet.

A general overview of a clinical trial carried out essentially entirely over the internet, in accordance with the method of the invention, is given with reference to the flowchart of FIG. 1, which illustrates an embodiment described in further detail in Example 1.

An on-line clinical trial is conducted from a central website 8, comprising home pages 14.

Use may be made of a search engine, browser, other internet access tool, or any other advertising medium or accessing a potential candidate database that increases the likelihood of an appropriate subject being provided with an opportunity to apply for participation in the trial via the website 8. For instance, the clinical trial may be advertised to candidate participants by various advertising strategies 10 (individually, 10a, 10b, etc.), including the internet (e.g. ads in health- and non-health-related web site) and, as desired, various other non-internet media (e.g., ads on TV, health magazines or newsletters, general interest magazines, or magazines relating to the internet). The effectiveness of each particular advertising strategy 10 can be gauged by directing interested individuals to a different web page in each advertising strategy, each such web page acting as a gateway 12 (individually 12a, 12b, etc.) to the clinical trial's home pages 14. Each gateway web page 12 can include a counter to record the number of 'hits', and records Internet Protocol (IP) addresses so that it can be determined which advertising route was used by a clinical trial participant to arrive at the home pages 14. This determination can also be achieved through other electronic means, such as cookies and URL-tags which are attached when an individual is directed to our site from a search engine. (Participants who did not access the trial's website through one of these gateways are classified as having found out about the trial independently of any of the advertising strategies used for the given trial). The yield of each advertising strategy 10 can thus be measured.

To apply, the potential applicant is provided with a 'link' button within the homepages 14 to begin the application process.

Candidates are screened in a step 16 for their eligibility directly over the internet, via interactive questionnaires, as described later, which can be self-administered and allow 'self-diagnosis', that is, self-identification as having a medical condition or symptom(s) for which the test substance's effectiveness in treating is being tested. Candidates are pre-qualified by a hierarchical analysis of their response, as established by the investigators, much as is done in face-to-face interviews. The analysis can occur by use of computer-driven algorithms developed to rank the information generated from the candidate's response. Candidates who are determined to be preliminarily eligible or pre-qualified by their answers to the questionnaires, are each authenticated and their informed consent is obtained, as shown in step 18 of FIG. 1, by, e.g., mail, telephone, and/or electronic means. Such confirmation can include, as shown in step 20, review of additional questions and answers or external evidence (e.g., medical record or report, lab test, or X-ray), as needed. As shown in step 22, those qualified and selected for participation in step 20 may be contacted by telephone and are assigned a unique identifying code (e.g., user name) and a unique log-in password. Assignment of the identifier code and password includes them being individually or both chosen by the participant or given by a trial investigator or assistant. (For instance, a participant's email address may serve as his or her login name, and (s)he can designate his or own log-in password.) These are used, as shown in step 26, for accessing "protected information" at the clinical trial website, generally by internet. "Protected information" includes forms for evaluating the test substance's effectiveness and information generated about the participant and his/her health status from performing the steps of the on-line clinical trial method. Protected information also includes updated information provided by the investigator(s) about any adverse experiences reported by other participants, whose identity is kept confidential or anonymous. Some information about the clinical trial may be provided by another medium (e.g., mail), as needed to preserve the confidentiality of each participant's information, or to the extent that a candidate/participant cannot retrieve or obtain the information by the internet. For instance, regular mail may be used to provide a unique identifier and/or log-in password to a candidate selected to participate in the trial, if the participant indicates (s)he is not the sole user of his/her email address.

Informed consent is also obtained from candidate participants, by various alternative ways as shown in step 18. For instance, candidates are given, and asked to complete, to authenticate, and to return a consent form having a portion allowing a candidate's consent to be given to participate in the clinical trial, and a portion that enables the trial's investigator(s) to contact the candidate's personal health care provider(s) (e.g., physician, nurse practitioner) to obtain the relevant medical information or record(s) that confirm the diagnosis of the candidate's medical condition (e.g., X-ray, lab test results, letter from the health care provider). A copy of the consent form is electronically accessible from the primary site, via the internet, and/or may be sent to a candidate participant by another medium (e.g., mail, fax, courier), as needed. The method of the invention also encompasses other means of obtaining and authenticating consent that are available, including existing internet means in which secure communication is established. The feasibility of a specific means for obtaining informed consent is limited only by the extent that it is acceptable to an ethical review board overseeing the ethics of a given clinical trial.

There exist many means or formats by which consent of a participant to participate in a clinical trial can be authenticated. Examples include but are not limited to: a hard (paper) copy of a written consent form signed by a participant; electronic authentication of a participant's consent (e.g, a unique digital signature or certificate registered to an identified user); a videotape recording of an individual's orally given consent; and some type of voucher or written confirmation of an individual's consent by a legally accepted authentication agency (e.g., a public notary's confirmation of a person's hand-written mark).

After a candidate participant is confirmed to be eligible for the clinical trial, (s)he is given instructions for reporting his/her symptoms directly over the internet, during the course of the trial, through a series of internet visits or virtual encounters 24 that are initiated through a login/password sequence 26. Generally there is a run-in phase for candidate participants to practice logging into the secure webpages 24 and completing and returning evaluation forms therein, and for investigators to withdraw candidate participants who do not comply with the trial protocol. After the run-in phase, compliant participants are randomized to receive either the test substance or a placebo. These trial substances are provided to the participant in whatever manner is convenient and suitable for a particular trial: e.g., by sending it by mail or by overnight courier directly to the candidate (step 27), or by enabling the participant to obtain it at a pharmacy or clinic accessible to the participant.

After commencing use of the trial substance, the participant reports his/her own symptoms directly to the clinical trial investigator(s) at least once, preferably on a regular basis, via questionnaires completed and transferred by the internet during the virtual encounters 24. The clinical trial is preferably conducted using multiple, scheduled 'online' visits to evaluate the effectiveness of the trial substance. In some cases, participants can provide certain data (e.g., demographic information, symptoms not directly used as a measure of a substance's effectiveness, etc.), at irregular or random times after commencement of the trial.

As well, a contact person is provided, whom participants may contact, e.g., by telephone, with their questions or health concerns, as necessary to provide a back-up and a comfort measure to participants. The participants' data are collected, validated, and stored centrally in a secured computer database 28 managed by at least one trial investigator(s) and/or agent of the investigator.

Figure 2:
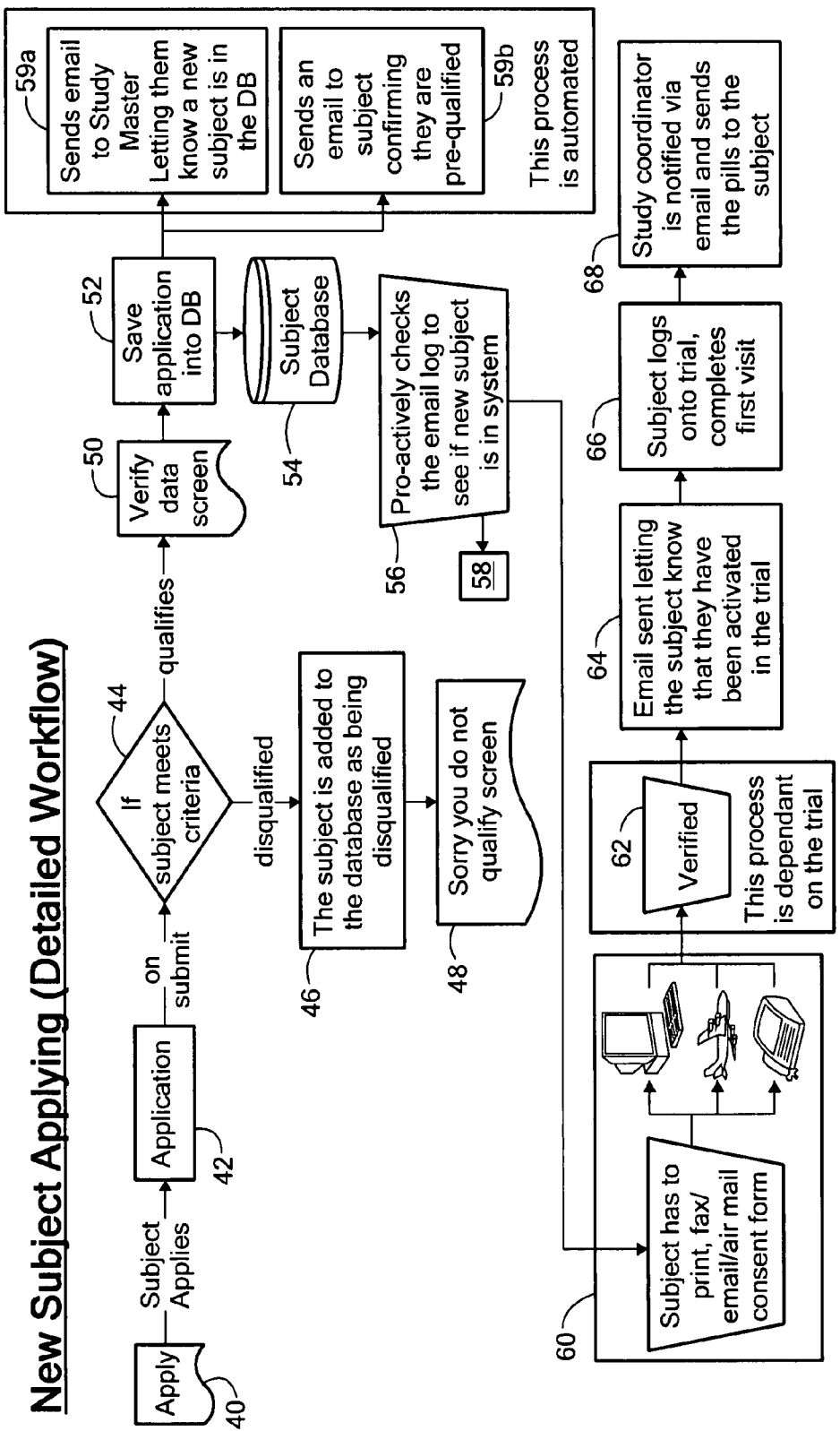
FIG. 2 is a flowchart of the steps involved in processing an applicant to an exemplary online clinical trial.

The application and qualification process is shown more completely in FIG. 2 where the applicant, after being persuaded by solicitation procedures to begin an application process in step 40, fills out an application form 42 and submits it over the internet in a step 40. An initial evaluation is undertaken in step 44 to verify that the form is properly filled out and the candidate meets certain prima facie criteria that the researchers have established. A failure to meet these criteria dumps the applicant's name into the database 28 in a step 46 and a form notifying the applicant of a rejection is emailed in step 48.

If the prima facie qualification of a candidate is made, then the preliminarily qualified candidate has the application verified or is noted as a qualified candidates in step 50 and his or her information is stored in database 28 at step 52. The candidate is placed in an candidate or subject file 54 of the database 28. The file 54 is checked by software processing in a step 56 to determine if new candidates are already identified as applicants in an email log 58. The candidate, now participant, is notified along with one or more of the investigators in steps 59a and 59b.

If a confirmation is made, then processing proceeds through consent-obtaining steps 60, through which the candidate receives a consent form and completes it, sending it back via email, mail, fax or other means to the main site, where it is verified and accepted in a step 62 if completed correctly and satisfactorily according to criteria dependent upon the legal and ethical requirements applicable to the particular trial.

The verified and qualified participant is sent an email in a step 64 that causes him/her to log in for a first visit and the completion of a form for that purpose, to start the data generation for the trial. With that form sent back to the central or primary site in step 66, the participant is then given or sent, in a step 68, a supply of the preparation, drug or placebo, that is being tested in the trial.

Figure 3:
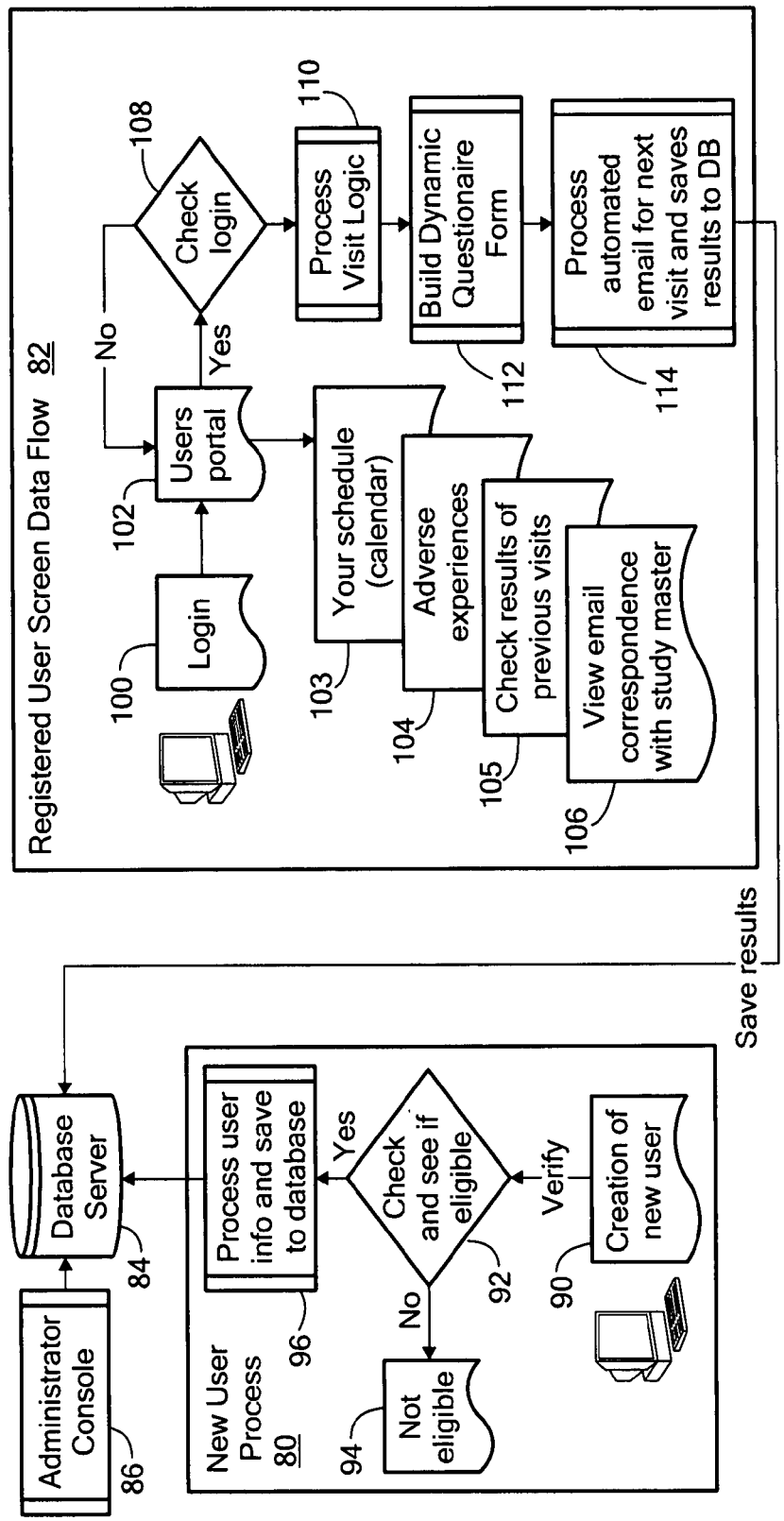
FIG. 3 is a flowchart of the overall information flow in a website for an exemplary online clinical trial.

FIG. 3 shows the data flow for initial information at both the central site 80 where the trial is being administered and monitored and an individual user's remote site 82, where the data is generated. A server 84 for the database 28 interfaces with the research or investigative staff through a console 86, to run the processing 80 of a new applicant through a basic, applicant input data file set-up step 90 (creation of new user) and through an eligibility test 92, with the applicant's information being saved either in a 'not eligible' file 94 or a file process 96 for eligible candidates.

The eligible, verified participant interfaces with the online trial through the user console or PC 100. The user console 100 has associated with it in storage, a user portal or interface 102 that contains and creates information on the user's virtual visit schedule 103, record(s) 104 of adverse or negative reactions to the substance being taken, record(s) 105 of prior visit results that can be checked, and a channel 106 for the review of correspondence with a trial researcher or study coordinator.

Each time a user or participant signs or logs into the central site, a login and identity check 108 is made using passwords and other security measures. The login step 110 sets up the system to receive data either as questionnaires filled out on line or as forms submitted as email attachments. As participant data comes in, a static or dynamic questionnaire is built in step 112. A static questionnaire would be one with preset, unchanging questions. A dynamic questionnaire allows additions to or modifications of existing questions, depending on the participant's answers, to be able to pursue certain questions in depth while others are given short shift. Once these data are assembled, they are stored for later analysis (or analyzed then) in steps 84-96. Finally, a new questionnaire is set up for the next visit which may or may not be based upon the results of the just completed questionnaire and/or prior results in step 114.

Figure 4:
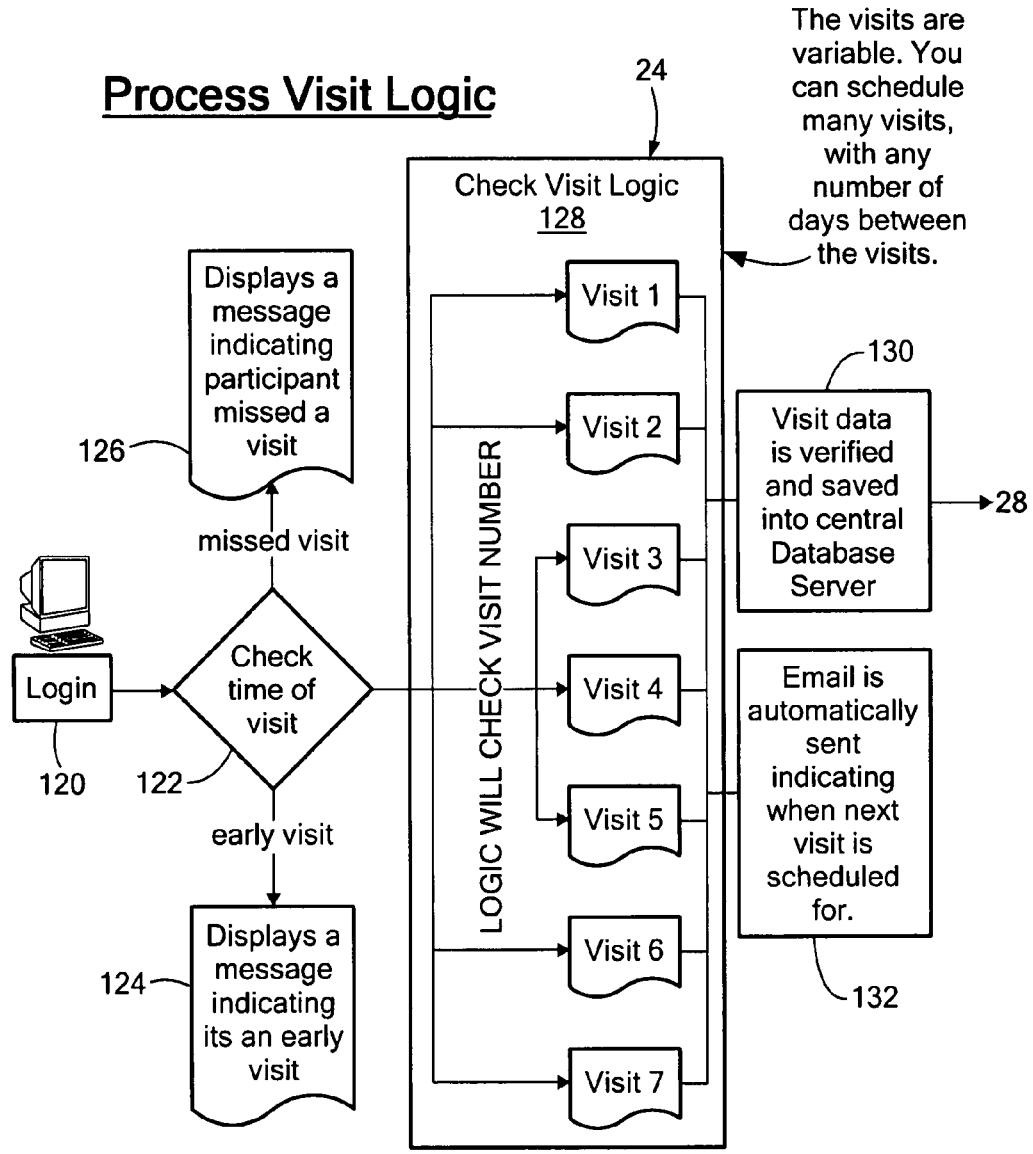
FIG. 4 is a flowchart of the processing of evaluative, virtual visits of a trial participant to the primary-site computer, via the internet.

FIG. 4 illustrates the processing of virtual encounters or visits 24 received from participants over the internet (via e-mail or in real time). The primary-site computer server processes a virtual visit by checking and recording the participant's login information in a step 120. A check step 122 processes visit login information for the timeliness of the visit questionnaire submission and flags an early response 124 or a missed response 126. If the timing of a visit response is then judged appropriate for use in the trial, it then goes to a visit processing center where the questionnaire data is evaluated and verified against a standard in a step 130 and then is placed in the database 28 for analysis according to procedures the researchers have established. The participant is then advised by email of the next scheduled visit in step 132.

Figure 5:
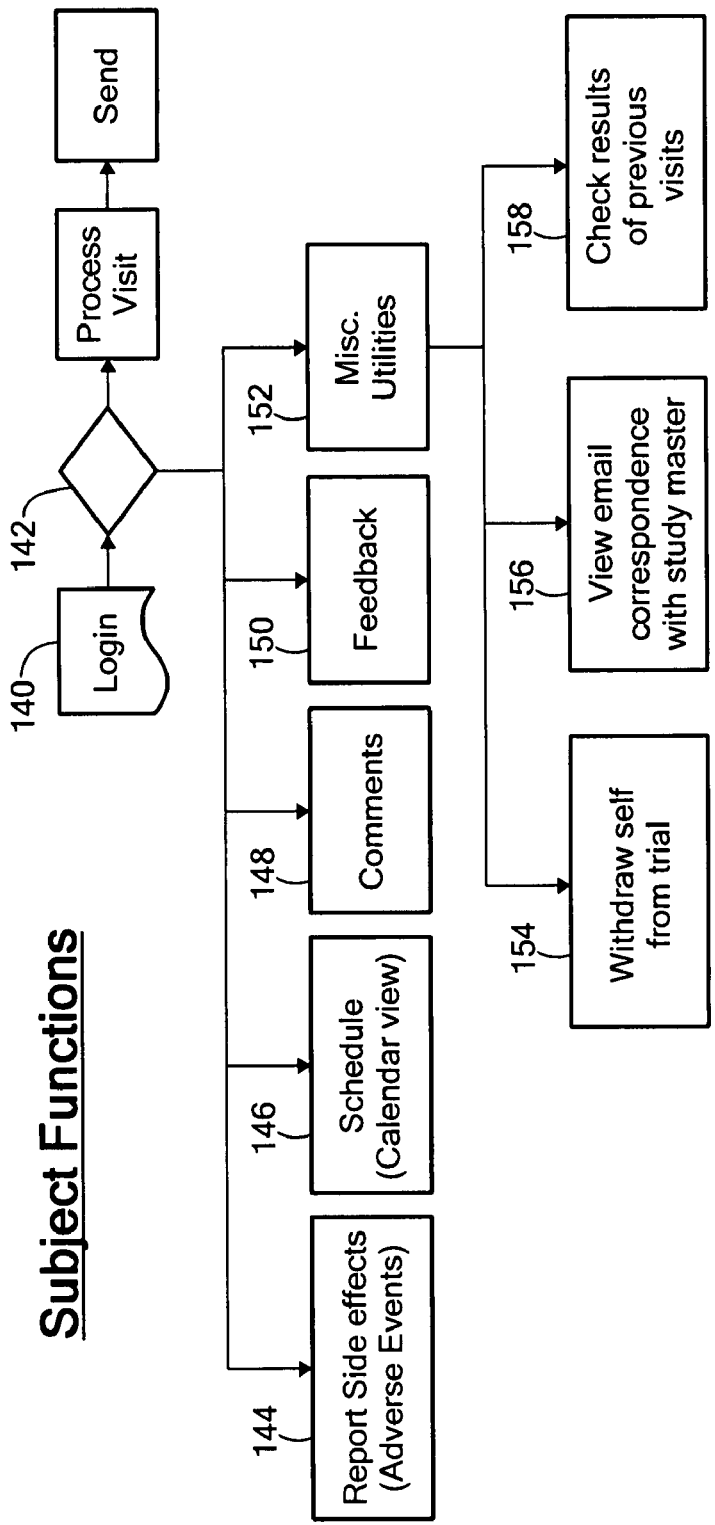
FIG. 5 is a flowchart of exemplary functions that can be performed by an online trial subject or participant from the participant's remote site.

FIG. 5 illustrates various functions that can be performed by a clinical trial subject or participant from the participant's site, commencing with the login process 140, after which the participant is allowed to access various questionnaire or dialog functions, including the generation of a report of side effects 144 and other phenomenon, a calendar 146 for viewing and/or scheduling a next or future visits, comments 148 regarding other matters that the participant feels should be addressed, feedback 150 from the researcher assigned to the participant, and access 152 to other, miscellaneous utilities. The other utilities include access to a form to withdraw from the program (154), access to prior email correspondence with researcher for review (156), and access to prior visit results for review (158).

Figure 6:
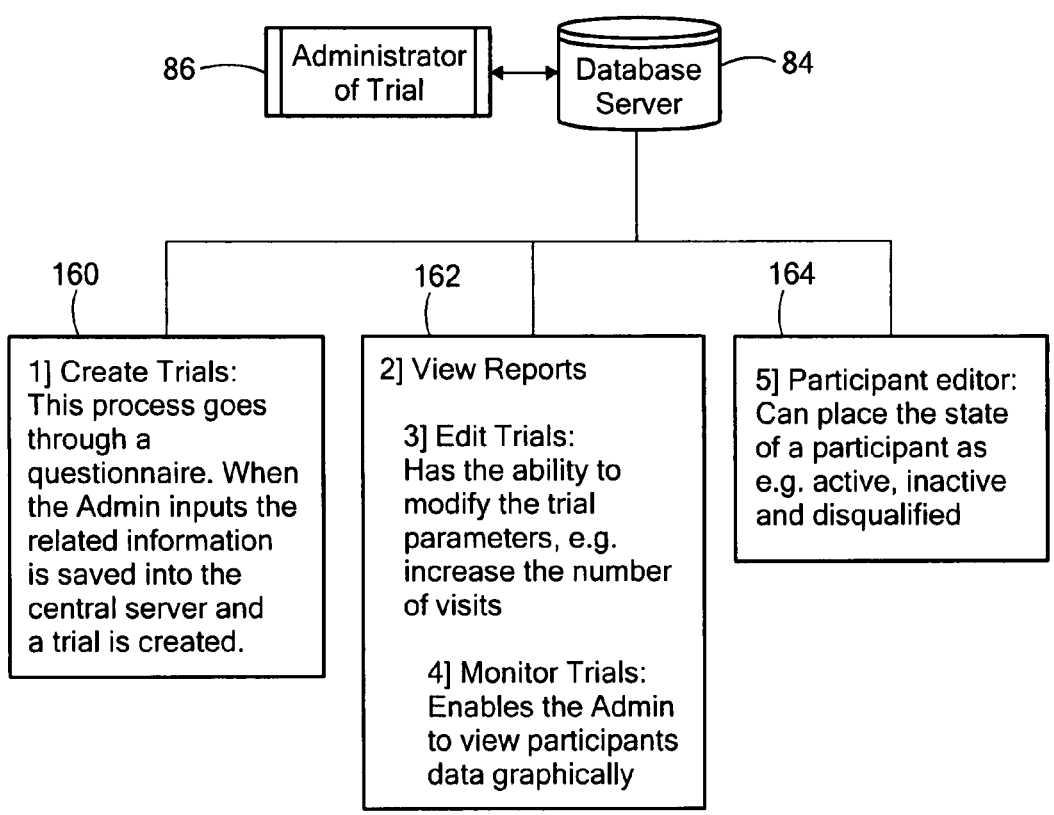
FIG. 6 is a flowchart of the functions that can be performed by the study master or principal investigator in the administration of an exemplary online trial.

FIG. 6 shows stages in the administration by the study coordinator or principal investigator of a trial at the central site administrator's console 86 and the accessible server 84. The administrator's software functions includes a trial creation function 160, which assembles the necessary questions into a series of questionnaires for the purposes described above and places them for storage in the server 84, linked to other software functions that need to access them in the process of participant qualification and evaluation of trial visits. A report function 162 allows the administrator to make adjustments in the questionnaires or their timing during the trial and to present data in raw or analyzed form in a variety of formats such as graphically. A participant whose responses are deemed problematic or who is rehabilitated, for any number of reasons, can be placed in an inactive, dropped, or reactivated state in functional area 164, which will cause that participant's data to be dropped or reinserted into the trial, as appropriate.

Figure 7:
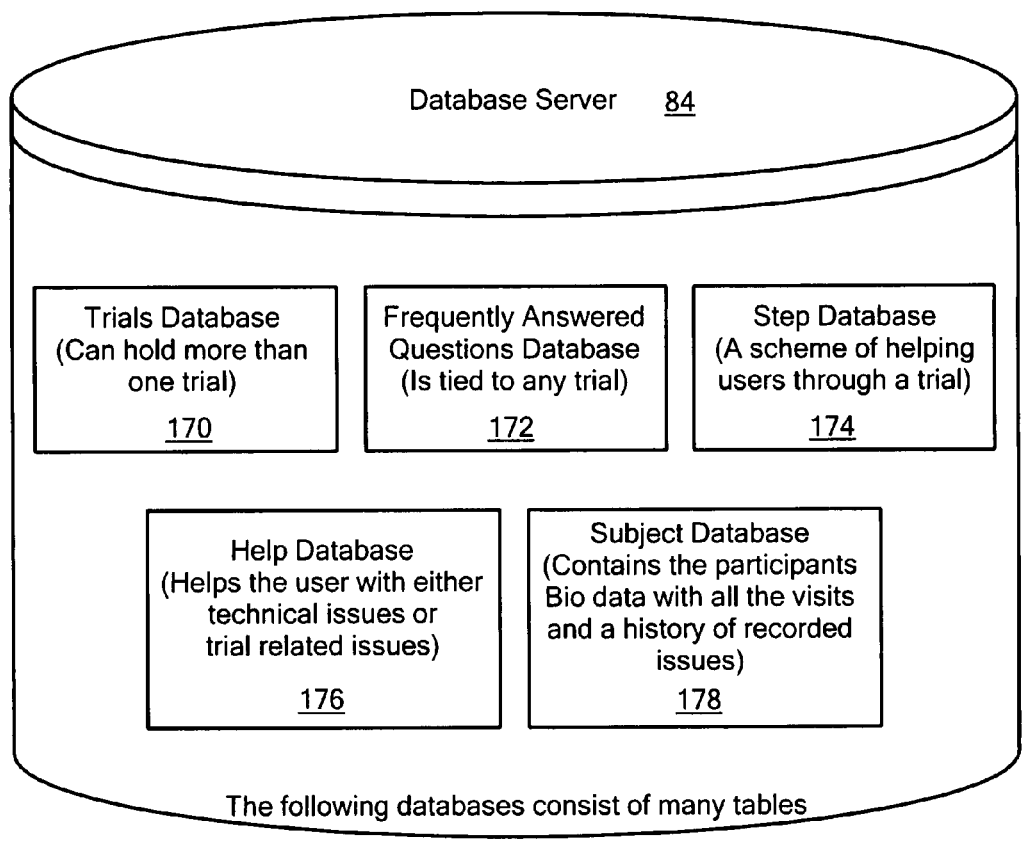
FIG. 7 depicts a database design for a clinical trial.

FIG. 7 shows how the database server is established with areas of specific functionality for use in trials generally. These include the trials database 170 for storing records from one or more clinical trials, files 172 of frequently answered questions for automated responses to participant inquiries, a step database 174 that guides participants through a trial, a general help file 176 for helping participants with technical issues or trial-related issues, as is known in the art, and a subject database 178 for the participant-created biographic and visit data. Each database can contain multiple tables or records.

As mentioned, the invention also encompasses using the internet to conduct only portions of a clinical trial, particularly the monitoring or evaluative phase. Thus, in a broad aspect, the present method of conducting a clinical trial of a test substance over the internet from a primary internet site, comprises the following steps:

providing to at least one clinical trial participant located at a remote internet site distinct from the primary site, instructions on: using the test substance; accessing and completing at least one evaluation form from a website maintained at the primary site; and returning electronically said at least one evaluation form to the primary site;

providing said at least one evaluation form in electronic format for use by the participant, said at least one evaluation form having a question and answer section from which a determination can be made of one or more effects of the test substance on the participant completing the evaluation form;

compiling data regarding at least one said effect of the test substance on the participant, from information from a received and completed evaluation form returned by the participant to at least one investigator conducting the clinical trial. As used here, "at least one effect" can refer to no effect or no change in, or to one or more observable changes in, a conventionally accepted indication of a medical condition.

Additionally, the participant's informed consent to participate in the clinical trial is obtained, in any of a variety of ways, depending on the particular requirements of a clinical trial and on what is deemed by an ethical review board to be appropriate and/or legal, "informed consent", as that term is commonly understood in the medico-legal community. Current technology provides many means for recording and authenticating a consent given by an individual, including the use of handwritten signatures, facsimile copies, electronic or digital signatures, registrations, or certificates, or use of authentication agencies (e.g., public notaries). Use of any such technology is limited only by what is acceptable to an ethical review board.

Obtaining informed consent may be performed by sending, via the internet or other means, a blank consent form from the primary site to the remote site, and receiving at the primary site from the remote site, a completed consent form from the participant to participate in the clinical trial.

Obtaining informed consent may comprise causing a consent form to appear at the remote site, and providing for authentication of a consent form completed and returned by a candidate participant. Alternatively, obtaining the participant's informed consent can comprise sending a hardcopy of the consent form to the participant for completion and return to at least one investigator conducting the clinical trial. The latter may be needed, for instance, if a candidate participant cannot access an electronic copy of the consent form, or if an ethical review board requires informed consent to be in a physically signed copy of the consent form.

The consent form includes information about the clinical trial, a portion allowing consent to be given to participate in the clinical trial, and a portion allowing consent to be given to release of the participant's medical information to at least one investigator conducting the clinical trial. When electronically provided, the consent form is caused by a primary-site computer server to appear at the remote site computer in response to the primary site receiving from the remote site, either a request for the consent form, or a completed screening questionnaire. The questionnaire has portions for receiving information for use in making a determination of whether an individual upon whose behalf the questionnaire is answered, is eligible to be a participant in the clinical trial. Such information may be, for instance, details about one or more symptoms conventionally accepted by health care providers (e.g., doctors, nurses, psychologists), as clinical indicia of a given medical condition.

The on-line clinical trial method of the invention can further comprise, in addition to providing instructions and evaluation forms to participants over the internet, screening potential candidates over the internet for eligibility to participate in the clinical trial. Such screening comprises:

maintaining, at the primary site, the website 8 that is accessible from remote sites via the internet and that provides information about the clinical trial and minimum eligibility criteria for participants in the clinical trial;

transmitting a screening questionnaire over the internet to a remote site, after receipt, at the primary site, of a request from the remote site to display the screening questionnaire, wherein the questionnaire has portions for receiving a candidate's information that enables a determination of whether a candidate is eligible to be a participant in the clinical trial;

receiving the completed questionnaire at the primary site via the internet; and reviewing the received questionnaire and making a determination of whether the individual is eligible to be a participant in the clinical trial according to a set of predetermined criteria. The predetermined criteria have been selected by the trial investigation(s), and can include such parameters as: a threshold degree of a symptom or symptoms associated with the medical condition for which the test substance is being tested; country of residence; age; gender; racial or ethnic background; and other requirements dictated by the particular clinical trial.

More specifically, the method of conducting a clinical trial of a test substance over the internet, can be seen as comprising the following steps:

maintaining, at a primary site, a website that is accessible from remote sites via the internet and that provides information about the clinical trial and minimum eligibility criteria for participants in the clinical trial;

causing a screening questionnaire to appear over the internet at a remote site, after receipt, at the primary site from the remote site, of a request to display the questionnaire, wherein the questionnaire has portions for receiving information that enables a determination of whether a candidate, upon whose behalf the questionnaire is completed, is eligible to be a participant in the clinical trial;

obtaining the candidate's informed consent to participate in the clinical trial;

receiving the candidate's completed questionnaire at the primary site via the internet;

reviewing the received questionnaire and making a determination of whether the candidate is eligible to be a participant in the clinical trial according to a set of predetermined criteria;

after receipt of the candidate's informed consent by at least one investigator, causing information transfer between the primary site and the remote site for the purpose of confirming the existence, identity, and eligibility of the candidate to participate;

providing to at least one clinical trial participant located at a remote internet site distinct from the primary site, instructions on: using the test substance; accessing and completing at least one evaluation form from a website maintained at the primary site; and returning electronically said at least one evaluation form to the primary site;

providing said at least one evaluation form in electronic format for use by the participant, said at least one evaluation form having a question and answer section from which a determination can be made of one or more effects of the test substance on the participant completing the evaluation form; and compiling data regarding at least one said effect of the test substance on the participant from information from a received and completed evaluation form returned by the participant to at least one investigator conducting the clinical trial.

Other embodiments of the on-line clinical trial methods of the invention may further comprise causing information transfer between the primary site and remote site for the purpose of confirming the existence, identity, and eligibility of the participant. Such confirming is accomplished by performing at least one step selected from the group consisting of: interviewing the participant by telephone or in person; reviewing at least one medical record of the participant; interviewing a health care professional who has provided health care to the participant; and reviewing at least one communication from the health care professional to the at least one investigator regarding the health status of the participant.

One way of determining the eligibility of the participant to participate in the clinical trial is by comparing the participant's answers to the questionnaire with a reference standard comprising conventionally accepted indications of a medical condition for which the test substance's effectiveness in treating is being tested. It is preferred that the medical indicia are of a nature that can be quantified and/or numerically or quantitatively represented on an internet web page.

The method may further comprise, prior to compiling data regarding the at least one effect, causing delivery, under authority of the investigator, of the test substance to the participant.

Additionally, the method may further comprise collecting and storing at a secure site, accessible by at least one trial investigator and by the participant upon providing a log-in password, information from at least one member of the group consisting of: at least one evaluation form completed and returned by the participant to the at least one investigator; and a screening questionnaire completed and returned by the participant to the at least one investigator. The secure site may be the primary site hosting the website for the clinical trial.

In a preferred embodiment of the method, a unique identifier and a unique log-in password is assigned to the participant for accessing protected information from the primary site. The identifier and/or password may be chosen by the participant himself or herself or be given by the investigator (e.g., by means of a computer-randomized and assigned alphanumeric code).

The method also comprises monitoring at least one effect of the test substance on a clinical trial participant by reviewing a plurality of evaluation forms, discussed below, each completed during an online encounter 24 and returned by the participant to at least one investigator. Each of the multiple evaluation forms is provided electronically to the participant at predetermined, different times after the participant has commenced using the test substance. The method further encompasses repeating the described steps with multiple participants, and collecting and analyzing data generated by the multiple participants each completing and returning at least one evaluation form to at least one clinical trial investigator.

The method of the invention also comprises providing encryption for information transmitted between the primary site and the remote site via the internet. Encryption can be done of various pieces of information, including but not limited to, the questionnaire, the evaluation form, information provided by the participant in completing those forms, some portions of the instructions for participating in the trial, and the like.

Any effect(s) of the test substance on the participant is determined by comparing answers from at least one evaluation form completed by the participant after having used the test substance, with answers from at least one evaluation form completed by the participant prior to using the test substance. The evaluation form has questions eliciting answers that provide information about a medical condition that can be represented numerically and be subjected to statistical analysis. Information sought in an evaluation form may be a quantifiable measure of a symptom, such as, but not limited to, an analog visual pain scale.

The method further comprises determining, from the data compiled from received and completed evaluation forms from multiple participants, whether the test substance has clinical efficacy in treating a predetermined medical condition.

Determining the test substance's clinical efficacy may comprise comparing the compiled data from participants using the test substance, with data compiled from received and completed evaluation forms returned by participants using a placebo.

Finally, the invention also encompasses a computer system for conducting a clinical trial over the internet, comprising at least one computer at a primary site from which the trial is conducted. The at least one primary-site computer comprises means, e.g., program code, for accomplishing or performing the steps of the online clinical trial method disclosed herein.

The invention offers at least the following advantages:

(1) Clinical trial participants do not need to go to a test center to receive the test substance and to be monitored.

(2) Fewer staff persons and resources are needed to conduct an on-line trial, as compared to a conventional clinical trial that requires in-person evaluation of participants and that often involves multiple clinical sites and hence, duplication of staff and overhead costs.

(3) The online method allows for real-time checking and verification, by trial investigators and participants, of data and information generated during the conduct of the clinical trial.

(4) The online method makes it economically feasible to conduct a rigorous and controlled study of non-prescription or nutritional compounds.

(5) The online method provides for more standardized implementation of the trial protocol and minimizes inaccuracy introduced by any conduct or population variability between multiple test centers.

(6) In contrast to a traditional clinical trial setting, the online method provides the potential of more rapidly recruiting the numbers of participants needed to generate sufficient statistical power in a given trial, and/or recruiting greater numbers of participants, thus enhancing statistical power to answer the study question, to perform subset analyses, etc.

(7) The online method allows a researcher to pose evaluative questionnaires more frequently than in a traditional setting, increasing the quantity and precision of the data and enhancing the statistical power of a trial.

The method of the invention is further described by way of the following, non-limiting example.

EXAMPLE I

Osteoarthritis is a Public Health Problem

Osteoarthritis is a common age-related disorder, with radiographic changes present in the knees of over 10% of the population aged over 45 years, and which causes a substantial burden of disability and economic cost in the elderly. Its prevalence in the US is believed to exceed 60 million people, and the incidence of symptomatic knee and hip OA has been estimated at 200/100,000 person years. It is responsible for some 68 million work loss days per year, and for 70% of all hip replacements at a cost of $3 billion, in the US annually.

Despite its frequency in the population, therapeutic options in osteoarthritis are limited. Current treatment recommendations highlight analgesics especially acetaminophen. Non-steroidal anti-inflammatory drugs, widely used to treat osteoarthritis, have not been found to be superior to acetaminophen for relieving pain or disability. While acetaminophen and non-steroidal drugs have been shown to be more efficacious than placebo for remediation of symptoms in osteoarthritis, their efficacy is limited. Long term NSAID use is associated with a 10% risk of gastric or duodenal ulcer and also poses high risks of kidney disease and even central nervous system symptoms. Acetaminophen may cause long term renal and possibly, hepatic adverse effects in patients who use this drug regularly at high dose which is the current recommended regimen for osteoarthritis.

Other treatment modalities for OA include exercise and muscle strengthening, but data supporting the efficacy of these modalities are incomplete and compliance with exercise regimens over the long term is inadequate. Joint replacement surgery is effective in alleviating joint pain, but is performed only after years of pain and disability and may not return patients to their premorbid state of function. In short, new treatments for OA are badly needed, especially ones that have favorable toxicity profiles and/or might have the potential for affecting the long-term course of disease.

Glucosamine and Chondroitin Sulfate

There has been a dramatic upsurge in the use of Glucosamine And Chondroitin Sulfate for arthritis, which followed the publication of *The Arthritis Cure* by Jason Theodasakis and Brenda Adderly in 1997. This book became a New York Times #1 Bestseller. Substantial numbers of patients with knee osteoarthritis appear to be using these products already. The eagerness with which the general public has embraced these products, perhaps, reflects inadequacy of current medical treatment for osteoarthritis and a popular perception that the traditional medical community has been biased against the potential benefits of nutritional products. Several aspects of Glucosamine And Chondroitin Sulfate as potential treatments for osteoarthritis make them ideal agents to be tested in an online clinical trial. The fact that they are safe and widely available enables them to be administered by mail with little need for intensive supervision. The compounds' high level of interest to the public is likely to facilitate solicitation of participants into the trial. Third, they are likely to be forerunners of a number of 'nutriceutical' agents touted as being efficacious for osteoarthritis. The fourth motivation to include these compounds relates to the current NIH RFP (NIH-NIAMS-98-02) calling for a traditional trial of these agents. The availability of results from a traditional clinical trial of these substances offers a means of comparing and validating the results of the internet-based methodology of the Online Glucosamine Trial.

Safety of Glucosamine and Chondroitin Preparations

The issue of safety is a critical factor in a study in which the therapy to be tested is administered and monitored remotely over the Internet.

Thousands of patients have received some form of glucosamine or chondroitin preparation worldwide. There appear to be no major adverse events or fatalities from taking any of these preparations. The more rigorous controlled clinical trials of oral glucosamine and chondroitin preparations published as manuscripts in peer-reviewed journals include 400 participants taking oral glucosamine or chondroitin sulfate. These studies have shown minor or moderate adverse rates to be similar to those taking placebo, and substantially lower than those taking a non-steroidal anti-inflammatory drug. Reported adverse events have generally been gastro-intestinal in nature. The results of a recent double-blind placebo-controlled of glucosamine hydrochloride in 94 patients with knee OA also found similar identical rate (12%) of minor adverse symptoms in the glucosamine and placebo groups (J. Houpt, MD$^{XXXV}$. No major adverse events were noted. In addition there have been no reports of allergic reaction to these compounds occurring among those allergic to beef or shellfish. No hematologic abnormalities have been reported in the human studies of glucosane hydrochloride and chondroitin sulfate. Nevertheless, individuals taking anticoagulants are and will be excluded from the model online trial.

Limitations of Traditional Clinical Trials for Testing Nutritional Products

Because they are safe and relatively inexpensive, nutritional products would still be effective public health interventions for a common disease like osteoarthritis even if only modestly efficacious. In fact, there are a number of potential OA therapies suggested by epidemiologic and clinical studies that are safe and whose efficacy may be modest, or may be slow in onset. These include micronutrients such as vitamin E, vitamin C, vitamin D, and folic acid and vitamin $B_{12}$ containing nutritional products such as avocado/soybean oil, as well glucosamine and chondroitin sulfate. All of the compounds merit further testing in the context of clinical trials, yet a considerable number of participants is required in order to detect reliably, a modest but clinically important symptom difference between active and placebo treatment.

The difficulties involved in testing agents such as glucosamine and chondroitin sulfate in a traditional setting are illustrated by two recent placebo-controlled double-blind studies performed in North America (Das, Houpt). Das et al enrolled 72 participants and demonstrated only a modest, non-significant therapeutic effect from oral glucosamine/chondroitin combination using the WOMAC assessment instrument for knee OA symptoms. The study of Houpt et al similarly suggested only modest efficacy for glucosamine.

Trials of modestly efficacious compounds for osteoarthritis, however, need to assemble large numbers of participants in order to generate sufficient statistical power to measure a difference between treated and untreated groups. For example, power calculations based on the results from these two trials suggest that approximately 320 participants would be required for each arm of a clinical trial using the WOMAC as the primary outcome measure. Thus, taking drop-outs into account, over 1000 participants must be enrolled in order to test the efficacy of such compounds in a three-arm study (e.g. placebo vs. Glucosamine vs. Glucosamine/Chondroitin Sulfate combination). In a traditional setting, this requires a multi-center study with duplication of many resources and personnel, such as research nurses, coordinators, and investigators. Further costs are incurred through requirements for advertising and travel reimbursements to participants to enable them to attend each center. As a result, such a study costs millions of dollars. The logistics and cost of this size of study are potentially prohibitive. In the setting of traditional medical center-based clinical trials, these numbers limit both the number of potential therapies which can be studied, and the ability to compare different formulations and combinations.

Rationale for Using the Internet to Perform Clinical Trials of Nutritional Products There are many aspects of a study testing the efficacy of a nutritional compound for osteoarthritis symptoms which are highly suited to the Internet. These relate both to the characteristics of the disease, and to the nature of the compounds being tested.

Firstly, with 6 million users aged over fifty, there are likely to be many individuals with knee OA on-line. There are established validated methodologies with which to ascertain and confirm remote cases with knee osteoarthritis, based on symptom questions and radiographic appearances. Widely-used and validated self-administered questionnaires exist with which to measure osteoarthritis symptoms. In fact, these questions are currently considered to be the optimal outcome measures for knee osteoarthritis studies—ironically, many of the clinical features documented in traditional osteoarthritis clinical trials are of insufficient reproducibility to function reliably. The internet also offers the opportunity of participation to individuals who are remote from clinical centers and would not otherwise be able to travel to a clinical site.

The second aspect of this trial that facilitates its application over the internet is that the compounds being administered have a high degree of safety. As nutritional products, they are widely available for purchase by the general public in health food stores. The level of risk undertaken by a participant in this study will be equivalent to an individual purchasing these supplements from a store. While we will take certain precautions, and monitor participants for reported adverse events, the level of participant surveillance required is substantially less than would be required for an experimental drug.

These aspects of the present internet-based clinical trial offer considerable efficiencies by eliminating the need for multiple sites and personnel. Aspects of the technology can also be used to enhance the quality of data collection by building in real-time error checking. Since data will be transmitted directly to a database, the burden of data-entry for the investigators is also reduced. Thus, large studies of this nature could be conducted over the internet at a fraction of the cost of a traditional multicenter clinical trial. This could allow scientific evaluation of generations of other nutritional products, which might otherwise be prohibitively expensive.

A model on-line clinical trial is being conducted over the internet, which monitors the use by individuals with symptomatic knee osteoarthritis ("knee OA"), of a glucosamine/chondroitin sulfate nutritional supplement as the test substance. In summary, the following is done:

1. A website for conducting the on-line clinical trial, which is accessible via the internet, has been constructed and is being maintained at a primary site within the Boston University Medical Center. It provides a description of an internet-based or on-line clinical trial of a supplement, namely a combination of glucosamine hydrochloride and chondroitin sulfate, in the treatment of knee osteoarthritis. This website includes a solicitation for participants, and a screening questionnaire for knee osteoarthritis that uses questions validated as diagnosing or identifying the presence and severity of that condition in an individual answering those questions.
2. Advertisement of the on-line glucosamine/chondroitin trial website uses primarily four different venues: (i) advertisements, announcements, links, etc., at internet-based, health-related websites (e.g., Arthritis Foundation web site); (ii) advertisements, announcements, links, etc., on other, non-health related web sites; (iii) advertisements, announcements, etc., in non-internet, health-related media (e.g., Arthritis Foundation newsletter and other popular health journal); (iv) non-internet, non-health related media (e.g., advertisement in magazine relating to the internet).
3. Disease status is confirmed by the clinical trial investigator(s) and/or their agents obtaining copies of candidate participants' medical records and performing chart abstraction using a validated algorithm for determining knee OA.
4. Candidates who respond to the screening questionnaire over the Internet and are determined to be eligible, are placed into a 14-week, model, double-blind randomized trial of a glucosamine hydrochloride/chondroitin sulfate combination in pill form. Participants use primarily the internet to transmit information from the remote site at which they access the internet, to the primary site at which the trial website is based and through which the trial investigator(s) access the internet. Specifically, participants complete one or more evaluation form(s) containing validated pain assessment questions, submit daily analgesic use data and pill counts, and report any adverse event(s) or symptom(s) occurring after commencing use of the glucosamine/chondroitin supplement.
5. The investigator(s) collect and analyze the information generated from the completed and returned evaluation forms.

Privacy and Security Issues Arising from Use of the Internet as a Vehicle for Recruitment and Conduct of Clinical Studies There exists the potential for interception of information posted electronically, and interference with scripts and data stored on the server. However, security enhancements are built into modern browsers and networks.

First, information posted on forms can be electronically encrypted so that only the intended recipient can decode the data. Data encryption is available on the latest internet browsers and will be used to secure information submitted by participants over the internet.

Second, all forms subsequent to the introductory questionnaire can be sent using the allocated identification number without information which directly identifies the participant. Files stored on servers can be protected by electronic 'firewalls' which restrict access to designated users. This system is widely used in the Boston University School of Medicine server. It is implemented by means of unique login names, passwords and by the unique IP address of the user's computer.

Finally, participant data can be stored on a secure server, to which only designated individuals have access. All electronic data from the online trial are stored on a secure server in the Boston University School of Medicine. All information allowing direct identification of participants is omitted from these databases. These databases also only contain information of a non-sensitive nature: e.g., pain scores, pill counts. Safeguards are imposed to prevent tampering or accessing of these data by non-study personnel. All hard-copy information, including copies of medical charts etc., are stored in a locked filing cabinet in a locked office. The data are used for trial purposes only and will not be distributed to other parties without the participant's permission.

Screening Methodologies for Knee Osteoarthritis

There have been numerous epidemiologic studies of knee osteoarthritis from which considerable experience with case ascertainment strategies is available (recently reviewed by Felson DT[v]). Most studies have used some combination of a symptom question and radiography, ranging from obtaining radiographs for all participants[vi] to a two step system comprising a knee symptom question followed by selected radiography of those who screen positive on the first step[vii]. All of these approaches can allow case definition according to the American College of Rheumatology criteria for the classification of knee osteoarthritis[viii].

The screening approach adopted in a given study is predicated to some extent on its objectives. For example, the validity of epidemiologic observational studies may be compromised if any cases are missed. These studies need a highly sensitive screening methodology, and may need to perform mass radiography to detect all cases.

In recruiting cases for a clinical trial such as the present online glucosamine trial, sensitivity of a screening instrument is less critical. This is because participants are randomized to receive an intervention or a placebo. Thus, while false negatives (missed cases of knee OA) may limit the generalizability of a particular trial, they will not influence the validity of that trial's results. This is analogous to recruitment for traditional clinic-based trials, which rarely take steps to ensure that the participants are representative of clinic patients, let alone the general population. There are rarely (but not invariably) good reasons to believe that therapies found to be efficacious in one subset of the population should not be so in another demographic group. It is notable, for example, that the results of intervention studies performed among elite groups (e.g., Physicians' Health Study which has generated at least 112 publications) are frequently generalized to the general population[ix]. These considerations are obviously of great relevance to this proposal in which the demographic characteristics of the participants will be different than that of the overall population. This is also why the internet has greater applicability in the conduct of a randomized trial than in performing an observational epidemiologic study.

In the online glucosamine clinical trial, a two-stage screening strategy is used. The first step comprises a series of questions posed over the Internet based on validated algorithms.[x] The second step utilizes radiographic appearances, either directly, or abstracted from a radiology report by use of an algorithm validated by Oliveria et al in a study of osteoarthritis incidence in an HMO population[xi]. This algorithm uses a list of 'key words' appearing in the medical record or radiology report to classify an individual as having radiographic osteoarthritis.

Measuring Change in Osteoarthritis: the WOMAC Osteoarthritis Index

The Western Ontario and McMaster Universities (WOMAC) index for osteoarthritis is a tri-dimensional, disease-specific self-administered health status questionnaire (see Table 1)[xii,xiii]. It probes clinically important, patient relevant symptoms in the areas of pain, stiffness and physical function in patients with OA of the hip or knee.[xiv] The index consists of 24 questions (5 pain, 2 stiffness, 17 physical function) which can be completed by the patient in 5 minutes. The WOMAC index has high test-retest reliability for all scales, and validation studies have showed high correlations with other indices probing the same dimensions including MHIQ index, Doyle index, the Lequesne index and others[xii,xv]. Responsiveness has been tested in non-steroidal trials and each aggregated subscale score (e.g. pain) has been found to detect the effect of NSAIDs,[xvi] and to detect a clinically important statistically significant difference in efficacy between two NSAIDs[xvii]. WOMAC has been found to be more sensitive to change, than other measures of patient status in OA, including HAQ, AIMS, the Doyle index the Lequesne index and measures of walk time, range of motion (relative efficiency compared to other instruments being ≧1)[xvi,xvii,xviii]. It can be utilized in a site-specific fashion and has been shown to discriminate between outcomes in opposite joints in the same patients[xix]. The WOMAC has been recommended as a measure for assessing 'slow-acting' drugs in OA, and has been employed in two recently completed, conventional clinical trials of glucosamine and chondroitin for knee OA (personal communications from Das MD, and from Joseph Houpt MD, Dept. of Rheumatology, University of Toronto).

Bellamy et al have also developed, tested and validated a computerized version of the WOMAC visual analog scale instrument[xx]. The computerized instrument was depicted in a format very similar to the original version, with visual analog scales and cursors which could be moved by the mouse. Numeric values between 0 and 100 were generated corresponding to the placement of the cursor. The instrument was found to be easy to use, with participants completing the questionnaire within 15 minutes. Concordance with scores assigned on the paper instrument were excellent, as was criterion validity based on aggregated subscale scores.

Tools for depicting and operationalizing internet-based visual analog scales are available for this online trial, and have been used to construct a computerized WOMAC questionnaire as described by Bellamy[xx]. Since most published WOMAC clinical trial data utilizes the visual analog scale version, the pain subscale of the WOMAC version VA3.0 is used as the 'primary' outcome measure in this model online glucosamine trial.

TABLE 1

The WOMAC Questionnaire[xv]*
WOMAC A (pain subscale)

The following questions concern the amount of pain you have experienced due to arthritis in your knee(s). For each situation please enter the amount of pain experienced in the last 48 hours.
   How much pain do you have?
      A1) Walking on a flat surface
      A2) Going up/down stairs
      A3) At night, while in bed
      A4) Sitting or lying (At rest)
      A5) Standing upright

*responses are indicated on a 10 cm visual analog scale by the respondent

Online Glucosamine Clinical Trial Web Site

Webpages have been created and posted within the Boston University Medical School Website. These pages are capable of providing information, obtaining consent and collecting preliminary data onto an ASCII file database. They can be accessed through the medical school's homepage (http://www.bumc.bu.edu/—follow link under 'Projects' to 'Arthritis Clinical Research'), or can be reached directly: http://etrials.bumc.bu.edu/. The pages provide information about the study ("Online Clinical Trial of Glucosamine for Knee Osteoarthritis"), and invite participation.

Specifically, a home page provides summary information about the on-line clinical trial—i.e., explains what is the test substance (glucosamine), why and how the trial is being conducted, the eligibility criteria for participants (e.g., age, U.S. residency, knee osteoarthritis, no diabetes, signed and returned consent form). The home page provides a link to another webpage with "frequently asked questions" (FAQs) and answers to those questions. The home page also provides 'links' to other pages with the screening questionnaire/ application form and the consent form, both of which are to be completed and returned by an applicant for participation in the trial.

The consent form presents information about participating in the trial in a 'question and answer' fashion, which can be printed and signed by an applicant, and sent by mail to the study coordinator. (Electronic completion and return of the consent form is a viable alternative, depending on the requirements of an ethical review board.)

Individuals who wish to determine their eligibility for the study are taken by a 'link' to an application form/screening questionnaire also posted at the website. The form asks questions about knee pain, osteoarthritis diagnosis, availability of knee radiographs, and use of analgesic medication. It also asks for demographic information and an Email address.

Information entered into the application form's fields and submitted to the computer at the primary site from which the trial is conducted, is added cumulatively to an ASCII file database located on the hard disk of that computer. The name of the remote computer submitting the information, and its IP address, are also obtained and saved in this database. Further refinements that have been or are being incorporated into these pages include automation of data collection, real-time monitoring of data quality (error checking and correction), generation of automated responses by Email, and programming devices (e.g. Java applet) to represent visual analog scales for the WOMAC questionnaires.

Publicizing Internet-Based Clinical Trials

Recruitment of candidate participants takes place using the internet, by way of a webpage dedicated to the "Online Glucosamine Trial". This page provides general information about knee osteoarthritis and guidelines for their management. It provides links to pages with further education resources, basic information about the clinical trial, and solicits participation.

The trial's web site is publicized using a variety of Internet-based and traditional strategies:
   (i) Internet-based, health-related (e.g. advertisements, links, on Arthritis Foundation web site)
   (ii) Internet-based, non-health related (e.g. advertisements, links, on other web sites)
   (iii) non-Internet, health-related (e.g. advertisement in Arthritis Foundation newsletter)
   (iv) non-Internet, non-health related (e.g. advertisement in Internet magazine).

Preliminary Screening of Individuals Expressing Interest in Participating in the Online Trial The trial's homepage directs individuals who are interested in participating in the study to a webpage with an application form, i.e., a knee osteoarthritis (knee OA) screening questionnaire (the Preliminary Eligibility Screen). It includes questions to be answered on-line by a candidate applicant, and a statement assuring confidentiality of the information provided by the applicant.

The screening questionnaire asks two questions (questions (1) and (2) below) that have been determined to perform best in screening for knee OA, particularly when combined with an x-ray to confirm the individual's health status. It also asks if the applicant has ever had a knee radiograph demonstrating evidence of knee OA; if the applicant takes medications regularly for knee pain; questions from the pain subscale of the WOMAC questionnaire for OA; questions regarding demographic variables including age, gender, race, occupational level, co-morbidities and co-medications; and country of residency.

For example, the eligibility screening page can display the following questions:
(1) Do you get pain in one or both knees after walking 2-3 city blocks (~¼ mile)?
_Yes _No _I am unable to walk 2-3 blocks
(2) Have you ever been diagnosed by a physician as having arthritis in your knees?
_Yes _No
(3) Have you ever had x-rays taken of your knees?
_Yes _No
(4) On most days, do you take medications for your knees?
_Yes _No
If yes, please indicate the sort of arthiritis medications you have been using:
_Tylenol _aspirin
_Other non-steroidal anti-inflammatories
    (e.g., ibuprofen, naproxen, Advil, Motrin, Alleve)
_Glucosamine or chondroitin sulfate preparations
_Multivitamins
_Other medications (please list): _

The eligibility screening/application form also provides a designated field for the applicant to provide additional comments regarding his/her condition. It also asks an applicant to disclose how (s)he found out about the trial's web site. Finally, the application form requests the applicant to provide the following items of personal information in designated fields: name; address; work and home telephone numbers; birth date; gender (optional); race (optional); occupation (optional); income (optional); email address. The email address is also used as the log-in identifier or name for an applicant selected to participate in the trial (i.e., a trial participant), for him or her to access the study's secure webpages. The applicant is also asked to enter and to re-enter, into a designated field in the application form, a personal password to be used to access the clinical trial. The webpage provides cursor-activated buttons by which the applicant can submit or reset the application form.

Participation is restricted to individuals resident in North America, preferably the United States. While the possibility of recruiting subjects from other countries has considerable appeal, the ethical and legal ramifications of doing so have not yet been fully worked out. Aside from using the country of residence as stated on the Preliminary Eligibility Screen form, the browser's IP address is used to determine or to verify an applicant's location. This reduces the potential for frivolous responses and the use of proxy participants within North America.

Applicants submit answers to the screening questions using the electronic form on the eligibility screening page, and receive a response from the study website indicating whether or not they have passed this preliminary eligibility screen.

Those who have passed the preliminary eligibility screen, and reside within North America, are directed to the consent form page (which also can be accessed separately for viewing, aside from the preliminary eligibility screen). Ineligible individuals are provided with information about further resources from whom information and counseling may be available (e.g., the Arthritis Foundation).

Authenticating the Identity of Candidate Participants

One of the major concerns in soliciting participation over the internet relates to the identity of the individual transmitting information. Although it seems unlikely that a person would assume another individual's identity in order to enter into a trial of a 'nutriceutical' (particularly without remuneration), the authenticity of the respondent's identity is important for reasons of confidentiality and obtaining valid informed consent. Therefore, steps are taken to confirm, as far as possible, the identity of the respondent, and that he or she is aged 21 years or over. All candidate participants are informed about the steps that will be taken before they submit any information to investigators.

As a first step, individuals who are interested in participating in the study are asked to submit their name, date of birth, address, telephone number(s), and email address (this occurs on the preliminary eligibility web page—i.e., the screening questionnaire). Each applicant is asked if (s)he is the sole user of the Email address provided in the screening form. Users who share an Email address will be sent confidential information, such as their login name and password, by surface mail. This is equivalent to the level of inquiry undertaken in traditional clinical trials settings, except that there will be no face-to-face contact. Provision of this information serves as a demonstration of interest in the study. Applicants who pass the preliminary eligibility screen are assigned a unique login name and password (e.g., by mail). These measures serve as a first step in reducing frivolous responses.

Corroboration of applicant's identities also occurs as a by-product of the process of validating their knee OA status, through communications between the trial investigators and the applicants' respective physicians and/or hospitals.

One further step is taken during the course of enrollment and determination of eligibility, to validate the identity of a candidate applicant. This occurs before any individual is provided with the trial compound and takes the form of a telephone conversation between the study administrator and the respondent. The candidate applicant will be informed that the objective of the call is to verify that (s)he is indeed the individual who expressed interest in the study over the internet, and that (s)he has continued interest in participating. (S)he is asked to confirm that these assertions are correct. Furthermore, channels are provided through which participants may make direct contact with the investigators on an on-going basis, including a toll-free telephone number and an Email address.

Other methods of authentication may be used, such as personal digital or electronic registration numbers or certificates, or use of authentication agencies.

Traditional clinical trials do not routinely require confirmation of identity, or request social security numbers unless payments are to be made. Potential recruits are often applicants to advertisements and frequently are unknown at the institution running the trial. Therefore, the risk of a participant's false identity exists even in the conventional clinical setting.

The internet-based glucosamine trial uses several measures to corroborate the identity of the respondent, which appear to be at least as rigorous as those employed in traditional clinical trials. In addition, the potential for frivolous or even malicious responses is further reduced by the facts that (i) no remuneration is provided to participants, and (ii) the investigative compound is of little interest to individuals in general other than those with OA.

Obtaining Informed Consent

Participants' informed consent to participate in the online clinical trial can be obtained as follows. A webpage is provided that post the consent form. Individuals who express a desire to participate in the study are asked to print out a hard copy of the consent form. (Individuals who do not have printing capability are able to request a consent form to be sent to them by mail.)

The consent form includes a detailed description of the online glucosamine trial. It also asks applicants for permission to write to their respective physician and/or hospital: (i) to obtain a knee radiograph or a copy of a knee radiography report (ii) to ask their physician to complete a short knee OA diagnosis checklist. The consent form contains language emphasizing its legal nature and asks applicants to confirm their identity. They are asked to sign the form in the presence of a witness, and to mail it directly to the study coordinator. Determination of a candidate applicant's eligibility and further data collection does not proceed until investigators receive an authenticated consent form.

Determining Eligibility for the Clinical Trial

Individuals eligible for this trial must be men and women aged over 50 years with symptomatic knee OA fulfilling the clinico-radiologic ACR criteria for the classification of knee OA (see Table 2)[viii], who consume analgesic medication on most days. The presence or absence of contributory features is determined by asking standard validated knee symptom questions over the internet, and by obtaining documentation of radiographic osteoarthritic changes (e.g., by obtaining the original radiographs or formal radiological reports).

Specifically, participants are required have symptomatic radiographic osteoarthritis of one or both knee joints, as determined in accordance with the ACR criteria, using (i) the response to the question "During the last month, did you have any pain or discomfort when walking 2-3 blocks (~¼ mile)?", and (ii) radiographic appearances (i.e. presence of osteophytosis).

The knee OA classification is contingent on applicants having had previous radiography of their knees. Radiographs, copies of radiographs, or copies of the radiographic report are requested from the institution and/or physician cited by the applicant as having performed the radiography. For logistical convenience, individuals who have never had radiography of their knees are ineligible for the trial.

Radiographs are scored for tibiofemoral and patellofemoral osteoarthritis using the individual radiographic features scoring system for the whole knee which we have previously tested and validated[xxi]. The radiologic criterion required by the ACR classification system is the presence of osteophytosis. When only a radiographic report is available, this is evaluated for mention of tibiofemoral or patellofemoral osteophytosis using the algorithm tested an used by Oliveria et al, which looks for the presence of certain 'keywords' in the chart or radiologic report[xi].

TABLE 2

ACR Clinical and Radiological Criteria for Classification of Idiopathic OA of the Knee knee pain
at least one of the following:

a) Age > 50 years
b) Stiffness < 30 minutes
c) Crepitus
osteophytes

Individuals are classified as having knee OA if they answer in the affirmative to the knee pain question, and have radiographs demonstrating OA changes with at least one osteophyte in the tibiofemoral or patellofemoral compartments (or equivalent on a radiographic report). As such, these individuals fulfill the clinical algorithm according to the ACR classification criteria for knee OA (see Table 3). In parallel with obtaining documentation of knee OA by means of participants' radiographs or medical reports, case validation is achieved by sending a short diagnostic checklist to each participant's physician for completion and return. This checklist asks for information documenting OA diagnosis and medication use (including other experimental compounds). The physician checklist approach has great utility in providing confirmation.

Participants are required to have undergone certain measures to verify their identity, and to have provided written, informed consent, including provision of addresses through which radiographs or their reports may be obtained. Tables 3 and 4 list the inclusion and exclusion criteria, respectively, by which participants are selected to participate in the online clinical trial.

TABLE 3

Online Clinical Trial Inclusion Criteria

1. At least one knee meeting clinico-radiologic ACR Criteria for Knee OA determined by:
   a) knee pain, defined as affirmative response to the standard question 'During the last month, did you have any knee pain or discomfort when walking 2-3 blocks (1/4 mile)?'
   b) age >50 years
   c) at least one area of tibiofemoral or patellofemoral osteophytosis seen on a radiograph or documented in a formal radiology report
2. WOMAC pain subscale score (range 0-500) of > 20
3. Report use analgesics for knee OA on most days
4. Willing to give written informed consent after an explanation of the study
5. Resident in North America

TABLE 5

Online Clinical Trial Exclusion Criteria

1. Identify contraindicated medical conditions (e.g., individuals taking anticoagulants)
2. Individuals taking medications with potential matric metalloproteinase-inhibitory properties (e.g. tetracyclines or structurally related compounds)
3. Individuals who received intraarticular injections in a knee joint within 60 days of Virtual Encounter/Online Visit 2
4. Individuals taking other agents claiming to possess disease/structure-modifying properties (e.g. avocado/soybean oil or glucosamine and/or chondroitin sulfate containing compounds)

Evaluation of OA Symptom Severity by Internet

To evaluate symptom severity in trial participants, an evaluation page is provided that includes the WOMAC questions, and a global pain severity scale, which appear as simulated visual analog scales, constructed by means of Java applets. Although these analog scales actually function as ordinal scales, by means of multiple small increments, they have been previously used to good effect in internet-based questionnaires (personal communication, Leslie Lenert MD, UCSF). Participants must enter their login name and password to access the evaluation page. Participants are prompted, by means of Email messages, to fill out the evaluation page at the requisite timepoints after commencement in the trial. The data submitted from this page by trial participants are collected into a separate ASCII database. This database can interface with a Microsoft Access program to facilitate data monitoring and analysis. The evaluation page includes a request for each participant to provide a count of residual capsules (test substance or placebo) in the bottle provided to each participant, as of the time at which (s)he is completing the evaluation page.

Exemplary evaluation pages are presented in FIGS. 8 and 9.

Enhancing the Characteristics of the Participant Sample to Include Compliant Participants: The Run-In Phase All eligible, candidate participants are each assigned a unique log-in name and password so that they can access the Evaluation Page via the internet. An on-paper pill diary is provided to participants so that they can keep a record of their analgesic use during the observation period. The Evaluation Page is used to collect data about symptoms, medication use, and weight at each 'virtual encounter' or 'visit'. Enrolled participants in the clinical trial are asked to access the page and conduct Encounter/Visit 1 (shown at FIGS. 8A-8C), which is the start of the 2-week run-in phase of the trial. Participants are asked to keep a record of their daily analgesic use on the paper pill diary, and to revisit the Evaluation Page exactly 2 weeks following Encounter/Visit 1. During this run-in period, they are encouraged to contact investigators, by Email or telephone, with any issues or questions that arise. A toll-free telephone number is provided to enable them to call investigators directly. Encounter/Visit 2 (shown at FIG. 9) represents the beginning of the actual treatment or substance usage period. The provision of the study pills is contingent on full and adequate completion of the Evaluation Page at both Encounter/Visit 1 and Encounter/Visit 2. Completion also includes the participant's provision of analgesic use data during the run-in phase, transcribed from his/her paper pill diary. The run-in phase: (i) serves as a familiarization and trouble-shooting exercise for participants with respect to data provision; (ii) allows selection of only those participants who are likely to remain compliant with the protocol into the treatment phase of the study; and (iii) establishes baseline values of the indicia of knee OA used in this trial, for outcome measures.

Provision of Study Capsules to Participants

Candidates eligible to participate in the trial are randomly assigned, in a double-blind fashion, to receive either the 'active' test substance, or a placebo. The 'active' test pills contain a combination of 500 mgs glucosamine hydrochloride and 400 mgs chondroitin sulfate. 'Active' and placebo pills are indistinguishable and identifiable only by a code number present on the label. The glucosamine/chondroitin and placebo capsules or pills are provided through the Boston Medical Center Pharmacy. The Boston Medical Center Pharmacy serves to store the capsules, to perform randomization, and to break codes as necessary.

Participants who adequately complete the initial, run-in phase of the study are randomized to receive 'active' treatment (glucosamine/chondroitin) or placebo. Randomization will occur after Virtual Encounter or Visit 2, which takes place at the end of the 2-week run-in phase of the trial. The results of the randomization are not provided to the investigators or participants. Participants are sent their capsules by, e.g., express mail, so that there is a delay between Encounter/Visit 2 and commencement of the study pills. Participants commence using the study pills soon after their receipt: two taken each morning and one taken each evening.

Clinical Trial Treatment Regime

Participants are asked to take three capsules per day for 12 weeks (two each morning and one each evening). They are asked to maintain use of the same type of class of analgesic during this period (as that type used prior to the clinical trial), although the frequency and dose may be altered as required. During this period, they must keep a daily record of analgesic consumption, including any change(s) in medication, and report any adverse event(s). They must provide responses to the pain assessment questions every two weeks by logging into the Evaluation Page. Email reminders are sent to them shortly prior to each anticipated virtual/online encounter or visit, to enhance compliance.

Outcome Measures and Use of Questionnaires for Reporting Responses

The primary outcome assessments for the clinical trial are: (i) the WOMAC VA3.0; (ii) global pain visual analog scores; and (iii) any change(s) in use of analgesics. These measures are being collected using the Evaluation Page, and being stored cumulatively in a database.

Measures to Enhance Continuing Participation and Compliance

A number of measures are being used that have been found in traditional, clinic-based studies to enhance compliance with a study protocol. These include establishing telephone contact with each participant, regular Emailed reminders and updates, and establishment of an open channel of communication between participants and the study coordinator using Email and a toll-free telephone number. In addition, minor incentives are offered for continued participation, such as study keychains, mugs, and magazine subscriptions. While being of little financial value, these measures have been found to increase participants' sense of connection with past longitudinal, observational studies.

Handling of Adverse Events

Glucosamine and chondroitin are classified as food supplements and are non-toxic. No serious adverse event has ever been reported for any participant in a study of these compounds, and reported side-effects of minor severity have occurred with equal frequency among those taking active compound and those taking a placebo. No allergies have been reported from oral consumption of these products. However, measures are taken to monitor any reported, unforeseen adverse event(s). Participants have the opportunity to report any perceived adverse events on their pill diary form. In addition, for events perceived by the participant to be of greater than minor severity, a toll-free telephone number is provided through which they may contact the study administrator or the principal investigator (P.I.). Randomization codes are and will be kept at the Boston Medical Center Pharmacy, which is open 24 hours per day.

Confidentiality and Security of Information Provided by Participants Over the Internet Measures have been adopted to ensure security of trial participants' data. First, each participant is assigned a unique identifier (e.g., username) and password to enable each participant to log into his or her own personal trial forms (e.g., screening questionnaire, evaluation form(s)). The identifier and code is sent by surface mail to prevent the possibility of its interception as an Email message. The username is preferably a pseudonym so that the participant's actual name, or other identifying features, will not be present in the trial database. If an email address is used as a log-in name, then an additional identifier can later be assigned to each participant record in the trial database once the trial and collection of participant data is completed, prior to analysis of the data by the investigators. The correspondence or match between each participant's log-in username and individual record identifier can be stored in a data file separate from the trial database.

The only other personnel with access to these forms is the principal investigator (P.I.) and the Website data manager. This measure prevents other individuals from accessing, or tampering with, a participants' information. By offering software adaptations, as necessary, encryption of data transmitted by each participant is facilitated by using the SSL protocol common to both Netscape Navigator and Microsoft Explorer. This will ensure that all data are transmitted in a form interpretable only to the study website. Third, all received data is stored on a secure server within the Boston University School of Medicine network. This network has high levels of internal security, with the ability to impose different levels of access to different sites based on an individual's access password. All access to the machine running the study over the Internet will be restricted to the http protocol. Users cannot and will not be able to run JAVA applets on the server or to access other software (such as electronic mail programs) that might allow them some ability to control the operating system. Computer Gateway Interface programs working with the http server (programs that work with the http server to provide additional functionality in WWW sites) will be limited to programs that work directly with the study database. Access to study data is confined to the P.I. and the website systems administrator.

There still remains a potential risk to participants, relating to tampering with or acquisition of data by unknown parties. Since the data that will be stored on the computer are relatively non-sensitive, it is unlikely that any great harm would befall a participant as a result of such an incident.

Documenting Compliance with the Study Protocol

Participants are asked to keep a daily record of consumption of study capsules as well as all concomitant analgesics or non-steroidal anti-inflammatory analgesics. They are requested to enter these data into fields on the Evaluation Page. These data function as an indicator of compliance with the study medication as well as a measure of analgesic requirements. Also, adherence to the study protocol is/will be evaluated for each participant by measuring: (i) the proportion of all questions which were adequately completed during the course of the study; and (ii) the proportion of participants who persevered until the end of the study (completion rate).

Performance of Symptom Evaluation Instruments on the Internet

Upon completion, the trial will provide a distribution of the answers to each of the symptom assessment questions administered on the Evaluation Page. This will include the global pain visual analog scale, the overall WOMAC scores, and the score of each WOMAC question item. Similar information obtained from traditional clinical and epidemiological studies are available for comparison with those obtained in this online trial.

Estimating the Cost of an Internet-Based Clinical Trial

Once completed, this online trial will provide an estimate of the cost of performing a fully powered clinical trial of nutritional products over the internet. It will include an extrapolation of the item costs involved in performing the proposed study, including utilization of the most efficient advertising strategy, as well as personnel, software and hardware costs. It is assumed that a fully powered clinical trial will require approximately 320 completers per trial arm. The numbers projection will also include an adjustment for drop-out and non-compliance rates found in this trial. Sensitivity analyses will be performed to accommodate variations in study design, such as multi-arm or factorial design approaches. The range of costs for this online trial will be compared with the costs of performing similar trials in a traditional, clinical setting.

Regulatory Issues

Glucosamine Hydrochloride and Chondroitin Sulfate are classified as nutritional supplements and are commercially available to the general public. Compliance with the Federal Regulations, 21 CFR 312.2, regarding the Investigational New Drug Exemption, has been documented to the Boston University School of Medicine Institutional Review Board, which has approved the present "Online Glucosamine Trial".

The trial compounds have been tested in many previous studies and are extremely safe. The risks associated with their use in this study, therefore, are similar to those of an individual obtaining them from a store. There remains, however, a potential for unforeseen events, as stated in the consent form, and provision is made for applicants to report any adverse event to an investigator by Email or telephone.

REFERENCES i Carey V J. Using hypertext and the Internet for structure and management of observational studies. Statistics in Medicine 1997; 16:1667-82 ii Houston J D, Fiore D C. Online medical surveys: using the Internet as a research tool. MD Computing 1998; 15:116-20 iii Kushi L H, Finnegan J, Martinson B, Rightmyer J, Vachon C, Yochum L. Epidemiology and the Internet (letter). Epidemiology 1997; 8:689-90 iv Kelly M A, Oldham J. The Internet and randomized controlled trials. Int J Med Informatics 1997; 47:91-9 v Felson D T. Epidemiology of osteoarthritis. In—Osteoarthritis, Eds Brandt K D, Doherty M, Lohmander S L. Oxford University Press, New York, 1998 vi McAlindon T E, Hannan M T, Felson D T et al. Are risk factors for patellofemoral and tibiofemoral knee osteoarthritis different? J Rheumatol 1996; 23:332-7 vii McAlindon T E, Cooper C, Kirwan J R, Dieppe P A. Determinants of disability in osteoarthritis of the knee. Annals of the Rheumatic Diseases 1993; 52:258-262 viii Altman R, Asch E, Bloch D, Bole G, Borenstein D, Brandt K, Christy W, Cooke T D, Greenwald R, Hochberg M et al. Development of criteria for the classification and reporting of osteoarthritis. Classification of osteoarthritis of the knee. Arthritis & Rheumatism 1986; 29(8):1039-49 ix Ridker P M, Cushman M, Stampfer M J, Tracy R P, Hennekens C H. Inflammation, aspirin, and the risk of cardiovascular disease in apparently healthy men. N Eng J Med 1997; 336(14):973-9 x LaValley M P, McAlindon T E, Evans S R, Chaisson C E, Felson D T. Questionnaire screening for symptomatic knee osteoarthritis. Arthritis Rheum 1977; 40(suppl):S110 xi Oliveria S, Felson D T, Reed J I, Cirillo P A, Walker W M. Incidence of symptomatic hand, hip and knee osteoarthritis among patients in a health maintenance organization. Arthritis Rheum 1995; 38:1134-41 xii Bellamy N, Buchanan W W, Goldsmith C H, Campbell J, Stitt L W. Validation study of WOMAC: A health status instrument for measuring clinically important patient relevant outcomes to antirheumatic drug therapy in patients with osteoarthritis of the hip or knee. J. Rheum. 15:1833-1840, 1988.

xiii Bellamy N. Osteoarthritis clinical trials: candidate variables and clinimetric properties. J Rheum 1997; 24:768-78 xiv Bellamy N, Buchanan W W. A preliminary evaluation of the dimensionality and clinical importance of pain and disability in osteoarthritis of the hip and knee. Clin Rheum 1986; 5:231-41 xv Bellamy N. WOMAC osteoarthritis Index: A user's guide. London, Ontario, 1995.

xvi Bellamy N, Buchanan W W, Goldsmith C H, Campbell J and Stitt L. Validation study of WOMAC: A health status instrument for measuring clinically-important patient relevant outcomes following total hip or knee arhiroplasty in osteoarthritis. J Ortho Rheum. 1:95-108, 1988.

xvii Bellamy N, Kean W F, Buchanan W W, Gerecz-Simon E, Campbell J. Double blind randomized controlled trial of sodium meclofenamate (Meclomen) and diclofenac sodium (Voltaren): Post validation reapplication of the WOMAC osteoarthritis index. J. Rheum. 19:153-159, 1992 xviii Griffiths G, Bellamy N, Bailey W H, Bailey S I, McLaren A C, Campbell J. A comparative study of the relative efficiency of the WOMAC, AIMS and HAQ instruments in evaluating the outcome of total knee arthroplasty. Inflam (In Press), 1994.

xix McGrory B J, Harris W H. Can the Western Ontario and McMaster Universities (WOMAC) osteoarthritis index be used to evaluate different hip joints in the same patient? J Arthroplasty 1996; 11:841-4 xx Bellamy N, Campbell J, Stevens J, Pilch L, Stewart C, Mahmood Z. Validation study of a computerized version of the Western Ontario and McMaster Universities VA3.0 osteoarthritis index. J Rheum 1997; 24:2413-5 xxi Felson D T, McAlindon T E, Anderson J J, Naimark A, Weissman B W, Aliabadi P, Evans S, Levy D, LaValley M P. Defining radiographic osteoarthritis for the whole knee. Osteoarthritis & Cartilage 1997; 5:241-50

What is claimed as the invention is:

1. A method of conducting a clinical trial of a test substance over the internet from a primary site, comprising the following steps:

assigning, at the primary site, a unique identifier and a unique log-in password to at least one clinical trial participant located at a remote internet site distinct from the primary site, the unique identifier and the unique log-in password for accessing protected information from the primary site;

providing to the participant, responsive to receipt by the primary site of the unique identifier and the unique login password, instructions on: using the test substance; accessing and completing at least one evaluation form from a website maintained at the primary site; and returning electronically said at least one evaluation form to the primary site;

providing, responsive to receipt by the primary site of the unique identifier and the unique log-in password, said at least one evaluation form in electronic format for use by the participant, said at least one evaluation form having a question and answer section, presenting at least one question, that when completed by a participant using the test substance, provides information regarding one or more effects of the test substance on the participant completing the evaluation form;

modifying, while the participant completes said at least one evaluation form in electronic format, said presentation of at least one question presented in said at least one evaluation form based at least in part upon one or more responses provided by the participant on at least one said evaluation form currently being completed by the participant and an evaluation form previously completed by the participant;

completing, by the participant, said at least one evaluation form; and compiling in an investigator accessible form data regarding at least one of said one or more effects of the test substance on the participant from information from at least one received and completed evaluation form returned by the participant to at least one investigator conducting the clinical trial.

2. The method of claim 1, further comprising obtaining informed consent from the participant to participate in the clinical trial.

3. The method of claim 2, wherein obtaining the participant's informed consent comprises sending a blank consent form from the primary site to the remote site, and receiving at the primary site from the remote site, a completed consent form from the participant to participate in the clinical trial.

4. The method of claim 2, wherein obtaining the participant's informed consent comprises:

causing a consent form to appear at the remote site, said consent form having information about the clinical trial, a portion allowing consent to be given to participate in the clinical trial, and a portion allowing consent to be given to release of the participant's medical information to at least one investigator conducting the clinical trial, and providing for authentication of the consent form.

5. The method of claim 4, wherein a computer server at the primary site causes the consent form to appear at the remote site computer in response to the primary site receiving from the remote-site, either a request for the consent form or a completed screening questionnaire, said questionnaire having portions for receiving information for use in making a determination of whether an individual upon whose behalf the questionnaire is answered, is eligible to be a participant in the clinical trial.

6. The method of claim 2, wherein obtaining the participant's informed consent comprises sending a hardcopy consent form to the participant for completion and return to at least one investigator conducting the clinical trial, said consent form having information about the clinical trial, a portion allowing consent to be given to participate in the clinical trial, and a portion allowing consent to be given to release of the candidate's medical information to at least one investigator conducting the clinical trial.

7. The method of claim 1, further comprising screening potential candidates over the internet for eligibility to participate in the clinical trial, the screening comprising:

maintaining, at the primary site, a website that is accessible from remote sites via the internet and that provides information about the clinical trial and minimum eligibility criteria for participants in the clinical trial;

causing a screening questionnaire to appear over the internet at a remote site, after receipt, at the primary site, of a request from the remote site to display the screening questionnaire, wherein the questionnaire has portions for receiving a candidate's information that enables a determination of whether a candidate is eligible to be a participant in the clinical trial;

receiving the completed questionnaire at the primary site via the internet; and reviewing the received questionnaire and making a determination of whether the candidate is eligible to be a participant in the clinical trial according to a set of predetermined criteria.

8. A method of conducting a clinical trial of a test substance over the internet, comprising the following steps:

maintaining, at a primary site, a website that is accessible from remote sites via the internet and that provides information about the clinical trial and minimum eligibility criteria for participants in the clinical trial;

causing a screening questionnaire to appear over the internet at a remote site, after receipt, at the primary site from the remote site, of a request to display the questionnaire, wherein the questionnaire has portions for receiving information that enables a determination of whether a candidate, upon whose behalf the questionnaire is completed, is eligible to be a participant in the clinical trial;

obtaining the candidate's informed consent to participate in the clinical trial;

receiving the candidate's completed questionnaire at the primary site via the internet;

reviewing the received questionnaire and making a determination of whether the candidate is eligible to be a participant in the clinical trial according to a set of predetermined criteria;

after receipt of the candidate's informed consent by at least one investigator, causing information transfer between the primary site and the remote site for the purpose of confirming the existence, identity, and eligibility of the candidate to participate;

assigning, at the primary site, a unique identifier and a unique log-in password to at least one clinical trial participant, the unique identifier and the unique log-in password for accessing protected information from the primary site;

providing, responsive to receipt by the primary site of the unique identifier and the unique log-in password, to the participant, instructions on: using the test substance; accessing and completing at least one evaluation form from a website maintained at the primary site; and returning electronically said at least one evaluation form to the primary site;

providing, responsive to receipt by the primary site of the unique identifier and the unique log-in password, said at least one evaluation form in electronic format for use by the participant, said at least one evaluation form having a question and answer section, presenting at least one question, that when completed by a participant using the test substance, provides information regarding one or more effects of the test substance on the participant completing the evaluation form;

modifying, while the participant completes said at least one evaluation form in electronic format, said presentation of at least one question presented in said at least one evaluation form based at least in part upon one or more responses provided by the participant on at least one said evaluation form currently being completed by the participant and an evaluation form previously completed by the participant;

completing, by the participant, said at least one evaluation form; and compiling in an investigator accessible form data regarding at least one of said one or more effects of the test substance on the participant from information from at least one received and completed evaluation form returned by the participant to at least one investigator conducting the clinical trial.

9. The method of claim 7 or 8, further comprising causing information transfer between the primary site and remote site for the purpose of confirming the existence, identity, and eligibility of the participant.

10. The method of claim 7 or 8, wherein the confirming is accomplished by performing at least one step selected from the group consisting of: interviewing the participant by telephone or in person; reviewing at least one medical record of the participant; interviewing a health care professional who has provided health care to the participant; and reviewing at least one communication from the health care professional to the at least one investigator regarding the health status of the participant.

11. The method of claim 7 or 8, wherein the eligibility of the participant to participate in the clinical trial is determined by comparing the participant's answers to the questionnaire with a reference standard comprising conventionally accepted indications of a medical condition for which the test substance's effectiveness in treating is being tested.

12. The method of claim 1, 2, 7 or 8, further comprising, prior to compiling data regarding the at least one effect, causing delivery, under authority of the investigator, of the test substance to the participant.

13. The method of claim 1, 2, 7, or 8, further comprising collecting and storing at a secure site accessible by the at least one investigator and by the participant, information from at least one member of the group consisting of: at least one evaluation form completed and returned by the participant to the at least one investigator; and a screening questionnaire completed and returned by the participant to the at least one investigator.

14. The method of claim 13, wherein the secure site is the primary site.

15. The method of claim 1, 2, 7, or 8, further comprising monitoring at least one effect of the test substance on the participant by reviewing a plurality of evaluation forms each completed and returned by the participant to at least one investigator, wherein each of the multiple evaluation forms is provided electronically to the participant at predetermined different times after the participant has commenced using the test substance.

16. The method of claim 15, repeated with multiple participants in the clinical trial.

17. The method of claim 1, 2, 7, or 8, repeated with multiple participants, and further comprising: assigning to each participant, a unique identifier and a unique log-in password for accessing protected information stored at the primary site; and collecting and analyzing data generated by the multiple participants each completing and returning the at least one evaluation form to the at least one investigator.

18. The method of claim 1, 2, 7, or 8, further comprising providing encryption for information transmitted between the primary site and the remote site via the internet.

19. The method of claim 15, further comprising providing encryption for information transmitted between the primary site and the remote site via the internet.

20. The method of claim 17, further comprising providing encryption for information transmitted between the primary site and the remote site via the internet.

21. The method of claim 1, 2, 7, or 8, wherein the determination of the at least one effect comprises comparing answers from at least one evaluation form completed by the participant after having used the test substance, with answers from at least one evaluation form completed by the participant prior to using the test substance.

22. The method of claim 16, further determining, from the data compiled from received and completed evaluation forms from multiple participants, whether the test substance has clinical efficacy in treating a predetermined medical condition.

23. The method of claim 17, further determining, from the data compiled from received and completed evaluation forms from multiple participants, whether the test substance has clinical efficacy in treating a predetermined medical condition.

24. The method of claim 22, wherein determining the test substance's clinical efficacy comprises comparing the compiled data from participants using the test substance with data compiled from information from received and completed evaluation forms returned to at least one investigator by participants using a placebo.

25. The method of claim 23, wherein determining the test substance's clinical efficacy comprises comparing the compiled data from participants using the test substance with data compiled from information from received and completed evaluation forms returned to at least one investigator by participants using a placebo.

26. A computer executable program code embodied on a computer readable medium, for conducting, with a processor and memory for said code, a clinical trial of a test substance over the internet from a primary site, comprising:

program code for assigning, at the primary site, a unique identifier and a unique log-in password to at least one clinical trial participant located at a remote internet site distinct from the primary site, the unique identifier and the unique log-in password for accessing protected information from the primary site;

program code for providing, via the internet, responsive to receipt by the primary site of the unique identifier and the unique log-in password, to at least one clinical trial participant located at a remote site distinct from the primary site, instructions on: using the test substance; accessing and completing at least one evaluation form from a website maintained at the primary site; and returning electronically said at least one evaluation form to the primary site;

program code for providing, responsive to receipt by the primary site of the unique identifier and the unique log-in password, said at least one evaluation form in electronic format for use by the participant at the remote site, said at least one evaluation form having a question and answer section including at least one question that, when completed by a participant using the test substance, provides information regarding one or more effects of the test substance on the participant completing the evaluation form; and program code for modifying, while the participant completes said at least one evaluation form in electronic format, at least a portion of the question and answer section included in said at least one evaluation form based at least in part upon one or more responses provided by the participant on at least one of said evaluation form currently being completed by the participant and an evaluation form previously completed by the participant; and program code for compiling into a central database at the primary site, investigator accessible data regarding at least one of said one or more effects of the test substance on the participant from information from at least one received and completed evaluation form returned by the participant to at least one investigator conducting the clinical trial.

27. The computer executable program code embodied on a computer readable medium of claim 26, further comprising program code for causing a consent form to appear at the remote site, said consent form having information about the clinical trial, a portion allowing consent to be given to participate in the clinical trial, and a portion allowing consent to be given to release of the participant's medical information to at least one investigator conducting the clinical trial.

28. The computer executable program code embodied on a computer readable medium of claim 27, further comprising program code for receiving and electronically authenticating a consent form completed and returned via the internet by the clinical trial participant.

29. The computer executable program code embodied on a computer readable medium of claim 26, further comprising program code for screening potential candidates over the internet for eligibility to participate in the clinical trial, including:

program code for maintaining, at the primary site, a website that is accessible from remote sites via the internet and that provides information about the clinical trial and minimum eligibility criteria for participants in the clinical trial;

program code for causing a screening questionnaire to appear over the internet at a remote site, after receipt, at the primary site, of a request from the remote site to display the screening questionnaire, wherein the questionnaire has portions for receiving a candidate's information that enables a determination of whether a candidate is eligible to be a participant in the clinical trial; and means for receiving the completed questionnaire at the primary site via the internet.

30. The computer executable program code embodied on a computer readable medium of claim 29, further comprising program code for reviewing the received questionnaire and making a determination of whether the candidate is eligible to be a participant in the clinical trial according to a set of predetermined criteria.

31. The computer executable program code embodied on a computer readable medium of claim 30, wherein the reviewing and determining program code provides for comparing the participant's answers to the questionnaire with a reference standard comprising conventionally accepted indications of a medical condition for which the test substance's effectiveness in treating is being tested.

32. The computer executable program code embodied on a computer readable medium of claim 30, further comprising program code for informing the candidate, via the internet, of the candidate's eligibility to participate in the clinical trial.

33. The computer executable program code embodied on a computer readable medium of claim 29, further comprising program code for causing information transfer between the primary site and the remote site for the purpose of confirming the existence, identity, and eligibility of the candidate to participate.

34. The computer executable program code embodied on a computer readable medium of claim 26, 28, 29, 32, or 33, further comprising program code for encrypting information transferred between the primary site and the remote site.

35. The computer executable program code embodied on a computer readable medium of claim 26, 27, 28, 29, 30, 31, 32, or 33, further comprising program code for collecting and storing at a secure site accessible by the at least one investigator and by the participant, information from at least one member of the group consisting of: at least one evaluation form completed and returned by the participant to the at least one investigator; and a screening questionnaire completed and returned by the participant to the at least one investigator.

\* \* \* \* \*